(12) United States Patent
Orenga et al.

(10) Patent No.: US 9,528,990 B2
(45) Date of Patent: Dec. 27, 2016

(54) FLUOROGENIC/FLUORESCENT PROBES DERIVATIVE FROM SULFOXANTHENE, AND USE THEREOF

(71) Applicants: bioMérieux, Marcy l'Etoile (FR); Centre National de la Recherche Scientifique, Paris (FR); Université de Rouen, Mont Saint Aignan (FR)

(72) Inventors: Sylvain Orenga, Neuville sur Ain (FR); Valérie Chalansonnet, Marcy l'Etoile (FR); Arnaud Chevalier, Paris (FR); Pierre-Yves Renard, Mont Saint Aignan (FR); Anthony Romieu, Mont Saint Aignan (FR); Benoit Roubinet, Mont Saint Aignan (FR)

(73) Assignees: BIOMERIEUX S.A., Marcy l'Etoile (FR); CENTRE NATIONAL DE LA RECHERCHE SCIENTIFIQUE, Paris (FR); UNIVERSITE DE ROUEN, Mount Saint Aignan (FR)

( * ) Notice: Subject to any disclaimer, the term of this patent is extended or adjusted under 35 U.S.C. 154(b) by 0 days.

(21) Appl. No.: 14/720,017

(22) Filed: May 22, 2015

(65) Prior Publication Data

US 2016/0146814 A1    May 26, 2016

(30) Foreign Application Priority Data

Nov. 26, 2014 (JP) ................................. 2014-238419

(51) Int. Cl.
C07D 491/18    (2006.01)
C12Q 1/44    (2006.01)
(Continued)

(52) U.S. Cl.
CPC ........... *G01N 33/573* (2013.01); *C09B 49/126* (2013.01); *G01N 33/542* (2013.01);
(Continued)

(58) Field of Classification Search
USPC ............ 546/41, 47; 435/19, 24, 28; 436/172
See application file for complete search history.

(56) References Cited

U.S. PATENT DOCUMENTS 8,828,678 B2 * 9/2014 Szczepanik ............ C09K 11/06
435/25

* cited by examiner

*Primary Examiner* — Charanjit Aulakh
(74) *Attorney, Agent, or Firm* — Oliff PLC

(57) ABSTRACT

The invention relates to fluorescent/fluorogenic probes of formula (I″) or (II″):

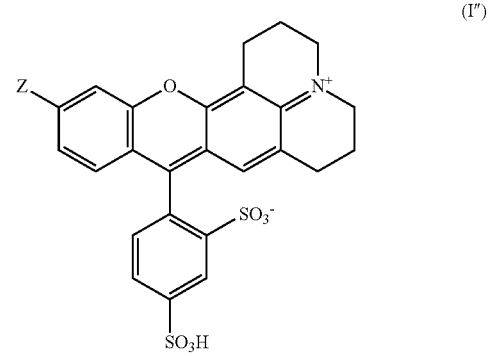

(I″)

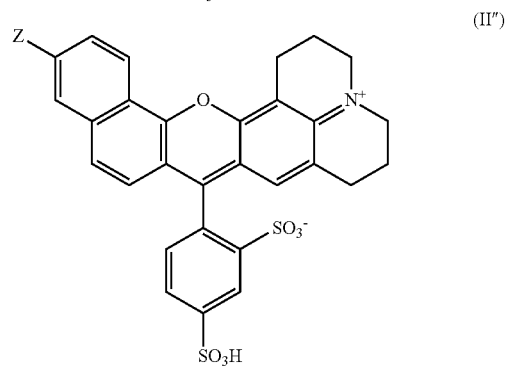

(II″)

wherein Z is chosen between:
—NH$_2$ and —OH,
or in the fluorescence quencher group consisting of:
—NO$_2$;
—N=N—R$^1$; R$^1$ being any organic group that does not obscure the corresponding azo bond;
—NHCO-Pept.; Pept. being a peptide residue or any organic group that does not obscure the corresponding amide bond;
—O-Glyc.; Glyc. being a oligoglycoside residue that does not obscure the corresponding glycosidic bond;
—O—C(O)—R$^2$; —O—P(O)(OR$^2$)(OR$^{2'}$) and —O—S(O)$_2$—R$^2$; R$^2$ and R$^{2'}$ being independently a hydrogen atom or an organic group that does not obscure the corresponding ester bond; and

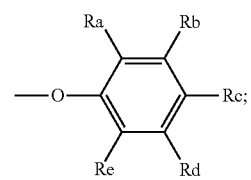

R$_a$, R$_b$, R$_c$, R$_d$ and R$_e$ being independently a hydrogen atom or any organic group that does not obscure the corresponding arylether bond so as not to prevent its possible cleavage by a myeloperoxidase activity.
It also relates to the use of these fluorescent/fluorogenic probes, for the detection of an enzyme activity, notably in order to identify/discriminate microorganisms in function of their ability to express particular enzyme activities.

21 Claims, 6 Drawing Sheets

(51) Int. Cl.
*G01N 33/573* (2006.01)
*C09B 49/12* (2006.01)
*G01N 33/58* (2006.01)
*G01N 33/542* (2006.01)

(52) U.S. Cl.
CPC ..... *G01N 33/581* (2013.01); *G01N 2333/902* (2013.01); *G01N 2333/908* (2013.01); *G01N 2333/90688* (2013.01); *G01N 2333/916* (2013.01); *G01N 2333/918* (2013.01); *G01N 2333/948* (2013.01)

FLUOROGENIC/FLUORESCENT PROBES DERIVATIVE FROM SULFOXANTHENE, AND USE THEREOF

The present invention relates to fluorogenic/fluorescent probes technology field, as well as to microbiology technology field. More particularly, it concerns microbial detection/identification testing and fluorogenic/fluorescent probes useful to detect/identify enzyme activities. It also relates to methods of detecting/identifying microorganisms in samples, wherein at least one step is dedicated to an enzyme activity screening.

In microbiology, detection and/or quantification of specific enzyme activities are very useful to discriminate microorganisms—for example a particular group, genus or species of bacteria—, for clinical purposes and/or for quality control considerations specific to some industrial sectors (e.g. pharmaceutical, cosmetic or food industries).

In this context, for last years, numerous enzymatic activity probes have been developed and implemented in reaction media, particularly fluorogenic/fluorescent probes.

Schematically, such fluorogenic/fluorescent probes consist in fluorogenic (i.e. non-fluorescent) molecules designed to act as synthetic substrates, more or less specific of targeted enzymes, and to be converted by the associated targeted enzyme activities to fluorescent reporter molecules whose optical properties can be detected/measured.

Hereafter Table 1 provides some known fluorogenic substrate/fluorescent probes.

TABLE 1

Examples of fluorogenic/fluorescent probes of prior art

| Fluorogenic substrates | Enzyme activities | Fluorescent reporter molecules (Fluorophores) |
|---|---|---|
| (disclosed in WO 00/28073) | nitroreductase | $\lambda_{abs/em}$ = 365/440 nm |
| CAS 596-09-8 | esterase (ethanoate esterase) | Fluorescein CAS 2321-07-5 $\lambda_{abs/em}$ = 497/520 nm |
| CAS 17817-20-8 Glyc. = galactosyl | glycosidase (β-galactosidase) | Fluorescein CAS 2321-07-5 $\lambda_{abs/em}$ = 497/520 nm |
| Molecular Probes ® bisamide derivative of rhodamine 110 (LIFE TECHNOLOGIES, USA) | peptidase | Rhodamine $\lambda_{abs/em}$ = 497/520 nm |

TABLE 1-continued

Examples of fluorogenic/fluorescent probes of prior art

| Fluorogenic subtrates | Enzyme activities | Fluorescent reporter molecules (Fluorophores) |
|---|---|---|
| CAS 133551-98-1<br>Glyc. = galactosyl | glycosidase<br>(β-galactosidase) | Naphtofluorescein<br>CAS 61419-02-1<br>$\lambda_{abs/em}$ = 600/670 nm |
| CAS 17833-43-1<br>Glyc. = glucosyl | glycosidase<br>(β-glucosidase) | $\lambda_{abs/em}$ = 360/449 nm |
| CAS 3368-04-5 | phosphatase | $\lambda_{abs/em}$ = 360/449 nm |
| CAS 1S220-11-8 | sulfatase | $\lambda_{abs/em}$ = 360/449 nm |
| CAS 17695-46-4 | esterase<br>(butyrate esterase) | $\lambda_{abs/em}$ = 360/449 nm |

In microbial identification testing, it is important to have a large diversity of available probes to cover the widest possible range of enzyme activities and to have the possibility to choose the probes to use, not only regarding the enzyme activity to detect but also regarding other parameters/criteria more linked to the probes themselves, for example their level of solubility/diffusion in a particular medium, their detection wavelength (excitation and emission wavelengths)...

In this context, the invention proposes a new family of fluorogenic/fluorescent probes, whose fluorescent reporter molecules provide an emission of fluorescence ($\lambda_{em}$) in orange, far-red and the near infra-red (about 550-750 nm). The fluorogenic substrate/fluorescent probes of the invention are especially useful for the detection of enzyme activity such as: nitroreductase, azoreductase, peptidase, glycosidase, esterase and myeloperoxidase activities.

These new fluorogenic/fluorescent probes are easy to synthesize and can advantageously be used in a large variety of reaction media routinely used for the detection of microorganisms, especially thanks to a good stability. Furthermore, for some of these fluorogenic substrates, their properties of solubility/diffusibility can be more or less tunable.

Before going further in the description of the invention, the definitions and the specifications below are given in order to facilitate the disclosure of the invention.

"Fluorogenic (enzyme) substrate" is understood to mean a non-fluorescent synthetic molecule when exposed to an excitation light energy of particular wavelength, and which may be modified by enzyme catalysis into a "fluorophore" (i.e. a fluorescent molecule), the fluorescence of which is optically detectable when said fluorophore is submitted to the same previously mentioned excitation light energy of particular wavelength. Said enzyme catalysis can involve one particular enzyme specific to the fluorogenic substrate, or different enzymes acting alone and similarly on the fluorogenic substrate, or several enzymes acting in combination on the fluorogenic substrate. To designate a fluorophore so-obtained from a fluorogenic substrate enzyme, the term "fluorescent reporter molecule" is also used.

The compounds of the invention (or probes), namely the fluorogenic substrates and the corresponding fluorescent reporter molecules can be observed in several ionization states, in accordance with the pH of the medium/environment in which they are implemented. Besides, said compounds of the invention may also be salified, that is to say they can exist and/or be prepared in the form of salts such as chloride, bromide, iodide, potassium or trifluoroacetate. For simplification purposes, the used chemical formulas representative thereof, as well as their description, do refer to one specific ionization state. The compounds of the invention are not limited to the specific ionization state here described.

"Reaction medium" is understood to mean a medium comprising the elements necessary for the expression of a metabolism and/or for the growth of microorganisms, of a cell or of an organelle. A reaction medium may be used in flow cytometry, histoenzymology, cell culture and the like, or as a medium for detection and/or identification of microorganisms. It may be solid, semisolid or liquid.

The expression "solid medium" is understood to mean for example a gel medium. Agar is the traditional gelling agent in microbiology for the culture of microorganisms, but it is possible to use gelatin or agarose. A number of preparations are commercially available, such as for example Columbia agar, trypcase-soy agar, MacConkey agar, Sabouraud agar or more generally those described in the Handbook of Microbiological Media (CRC Press).

A reaction medium may be a "detection and/or identification medium", that is to say a visualization medium, or a culture and visualization medium. In the first case, the microorganisms are cultured before inoculation and, in the second case, the detection and/or identification medium also constitutes the culture medium.

"Biological sample" is understood to mean a clinical sample, obtained from a sample of biological fluid, or a food sample, obtained from any type of food or a cosmetic or pharmaceutical or environmental sample obtained from any cosmetic or pharmaceutical preparation or from any environment. This sample may thus be gaseous, liquid or solid and there may be mentioned, without limitation, a clinical blood, plasma, urine or stool sample, samples from the nose, throat, skin, sores, cerebrospinal fluid, a food sample of water, drinks such as milk, a fruit juice; of yoghurt, meat, eggs, vegetables, mayonnaise, cheese; of fish and the like, a food sample obtained from animal feed, such as in particular a sample obtained from bone meal. The sample may also be taken from a clinical environment, a breeding environment or a food, cosmetic or pharmaceutical production environment. The expression sample taken from an environment is understood to mean in particular a surface sample, a sample of liquid, a sample of atmosphere, of raw material or of product.

The expression "sample" is therefore understood to mean the sample proper (swab, stool, food and the like) as well as colonies of microorganisms obtained from said sample (for example after isolation on a gel culture medium, or in an enrichment broth inoculated with said sample).

For the purposes of the present invention, the term "microorganism" covers bacteria, in particular Gram-negative and Gram-positive bacteria, yeasts, molds, and more generally organisms that are generally unicellular and invisible to the naked eye, which may be multiplied and manipulated in the laboratory.

"Organic group" is understood to mean a linear or cyclic hydrocarbon substituent, saturated or unsaturated. It includes substituents such as alkyls, alkenyls, aryls, cycloalkyls, cycloalkenyls and theirs derivatives (including oxygenated, nitrated, sulfured, halogenated, "metal" derivatives). An "organic group" can possibly be branched and/or functionalized (that is to say, it comprises at least one functional group such as: halogenated groups (fluoro, chloro, bromo, iodo), hydroxyl, thiol, carbonyl, aldehyde, esters (carbonate ester, phosphate, sulfate), amide, carboxylate/carboxyl, ether, sulfide alkyloxy, peroxy, amine/ammonium, pyridyl, phosphono . . . ).

"Alkyl substituent" is preferentially understood to mean a saturated hydrocarbon chain, such as, in particular, a $C_1$-$C_{20}$ alkyl, that is to say a linear or branched alkyl having from 1 to 20 carbon atoms. By way of example, there may be mentioned methyl, ethyl, propyl, isopropyl, butyl, t-butyl, pentyl, isopentyl and hexyl. "Aryl substituent" is preferentially understood to mean a substituent derived from an aromatic ring such as in particular an aromatic $C_6$-$C_{10}$ ring, in particular phenyl, benzyl, 1-naphtyl or 2-naphtyl.

The present invention is therefore directed to a fluorogenic or fluorescent compound of formula I" or II":

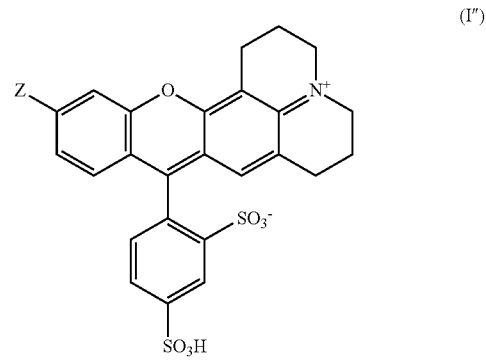

(I")

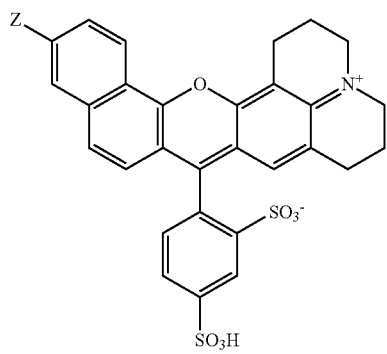

(II″)

wherein Z is a chosen between:
—NH$_2$ and —OH,
or in the fluorescence quencher group consisting of:
- —NO$_2$;
- —N═N—R$^1$; R$^1$ being any organic group that does not obscure the corresponding azo bond so as not to prevent its possible cleavage by an azoreductase activity;
- —NHCO-Pept.; Pept. being a peptide residue (a peptidyl without its terminal carbonyl moiety) or any organic group that does not obscure the corresponding amide bond so as not to prevent its possible cleavage by a peptidase activity;
- —O-Glyc.; Glyc. being an oligoglycoside residue that does not obscure the corresponding glycosidic bond so as not to prevent its possible cleavage by a glycosidase activity;
- —O—C(O)—R$^2$; —O—P(O)(OR$^2$)(OR$^{2'}$) and —O—S(O)$_2$—R$^2$; R$^2$ and R$^{2'}$ being independently a hydrogen atom or an organic group that does not obscure the corresponding ester bond (carboxylester, phosphoester or sulfoester bond) so as not to prevent its possible cleavage by an appropriate esterase activity (i.e. a carboxylesterase, a phosphoesterase or a sulfoesterase activity); and

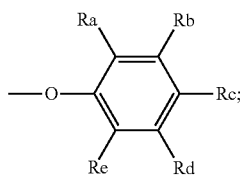

$R_a$, $R_b$, $R_c$, $R_d$ and $R_e$ being independently a hydrogen atom or any organic group that does not obscure the corresponding arylether bond so as not to prevent its possible cleavage by a myeloperoxidase activity.

The present invention is also directed to a particular use of such fluorescent/fluorogenic probes, for the detection of an enzyme activity, namely an enzyme selected in the group consisting of: nitroreductase, azoreductase, peptidase, glycosidase, esterase and myeloperoxidase activities.

In this context, a fluorogenic substrate of formula (I) or (II) is used:

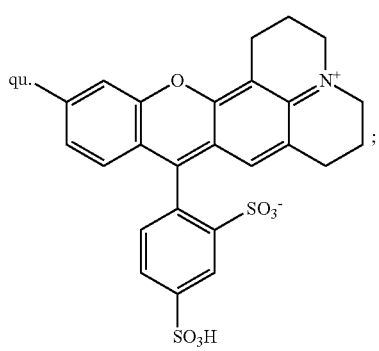

(I)

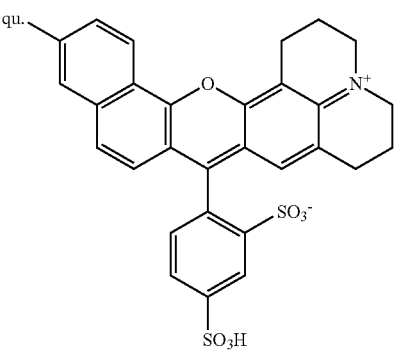

(II)

wherein qu. is a fluorescence quencher group as previously defined.

This fluorescence quencher group (qu.), constitutive of the used fluorogenic substrate, is chosen among the fluorescence quenchers, as previously listed, in accordance with the enzyme activity to detect. As a result, when this fluorogenic substrate is subjected to the appropriate enzyme activity, it forms a fluorescent reporter molecule of formula I' or II':

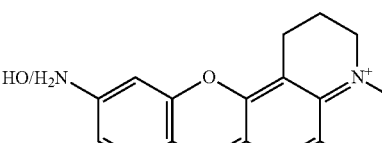

(I')

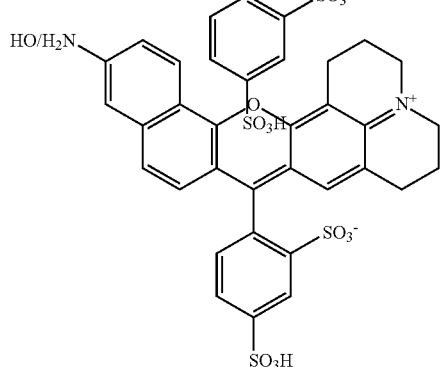

(II')

Such a use of a fluorogenic substrate of the invention can be advantageously carried out in the purpose to identify/ discriminate microorganisms in function of their ability to express the enzyme activity(ies) of interest. To this regard, the invention also relates to a method of detecting, in microorganisms, an enzyme activity selected in the group consisting of nitroreductase, azoreductase, peptidase, glycosidase, esterase and myeloperoxidase activities, comprising the following steps:

a) providing a reaction medium comprising at least one fluorogenic substrate of formula (I) or (II), as previously defined, b) inoculating said medium with a biological sample to be tested, c) incubating, and d) detecting the possible searched enzyme activity by a possible appearance or increase of a fluorescence, visible in the orange, far-red or near infra-red.

The present invention is also directed to a detecting agent, for detecting of an enzyme activity, namely an enzyme selected from the group consisting of: nitroreductase, azoreductase, peptidase, glycosidase, esterase and myeloperoxidase activities, wherein said detecting agent comprises a fluorogenic substrate of formula (I) or (II):

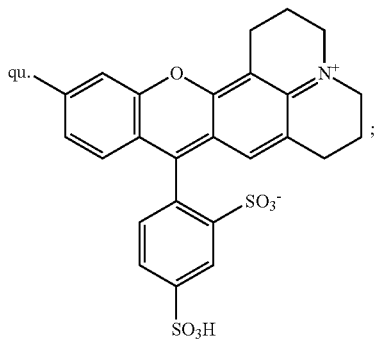

(I)

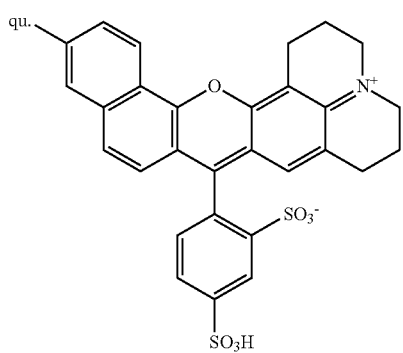

(II)

wherein qu. is a fluorescence quencher group as previously defined.

The present invention is thus based on the observation of interesting fluorescence properties of the following fluorophores, which derivate from sulfoxanthene and do correspond to compounds of formula I" or II", wherein Z is —NH$_2$ or —OH:

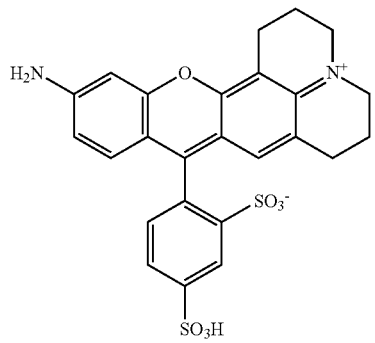

(SR101-110)

$\lambda_{abs}$ = 554 nm; $\lambda_{em}$ = 576 nm
estimated pKa ≈ 4-5; 27-29

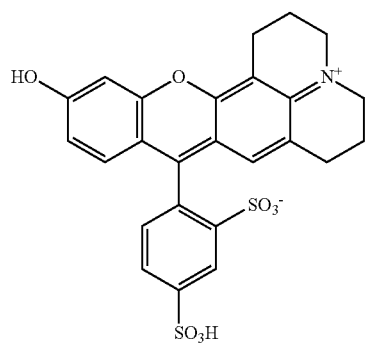

(SR101-OH)

$\lambda_{abs}$ = 548 nm; $\lambda_{em}$ = 572 nm
pKa ≈ 6.3

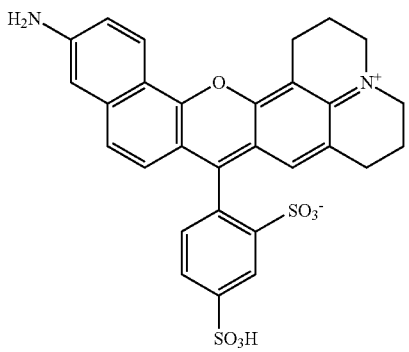

(SR101-NaphtNH$_2$)

$\lambda_{abs}$ = 546/589 nm; $\lambda_{em}$ = 625 nm
estimated pKa ≈ 4-5; 27-29

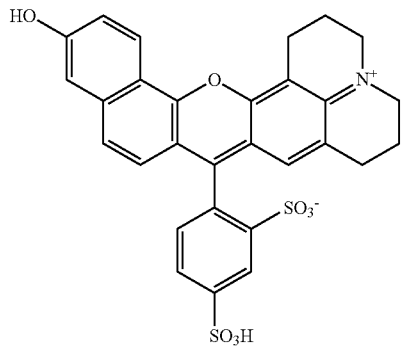

(SR101-NaphtOH)

$\lambda_{abs} = 537/580$ nm; $\lambda_{em} = 619$ nm
pKa ≈ 7.7

(the pKa values quoted for SR101-110 and SR101-NaphtNH$_2$ refer to respective acid-base couples RNH$_3^+$/RNH$_2$ and RNH$_2$/RNH$^-$).

These fluorophores were disclosed, for the first time, by the inventors, in "Chevalier A. et al., Chem. Eur. J., 2014, 20: 8330-8337".

The absorption and emission wavelengths, previously mentioned, are measured in a phosphate buffered saline, at 25° C.

From these fluorescent aromatic cores, a set of fluorogenic (i.e. non-fluorescent) enzyme substrates have been designed:

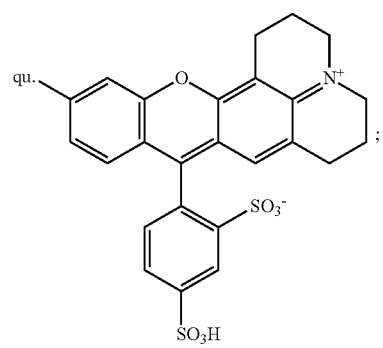

(I)

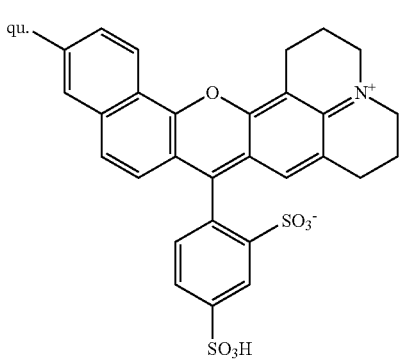

(II)

Each of them comprises a particular "fluorescence quencher group" qu., that:
when it is covalently bound to the aromatic core, modifies the electronic environment thereof so as to switch-off significantly its fluorescence, and
under an appropriate enzyme activity, is released from said aromatic core which recovers its —NH$_2$ or —OH function, and accordingly its fluorescence.

In this regard, it has been shown that a nitrate group (—NO$_2$) has the ability to disturb sufficiently the electronic environment of the aromatic core constitutive of a compound of formula I or II according to the invention, so as to quench/switch-off its intrinsic fluorescence. This fluorescence is then released on a nitroreductase activity. Consequently, a compound of formula I or II, as previously defined and wherein qu. is a —NO$_2$ group, can advantageously be used as a fluorogenic enzyme substrate for the detection of a nitroreductase activity.

Besides, it has also been shown that, like a —NO$_2$ group, any quencher group qu. can be envisaged for the preparation of fluorogenic substrates of formula I or II according to the invention, provided:

it involves a direct linkage with the corresponding aromatic core, it is chosen in the group consisting of: an azo bond, an amide bond, a glycosidic bond, an ester bond (including carboxyl ester, phospho(mono or di)ester and sulfoester) and an arylether bond.

The sole presence of such linkages directly on the considered aromatic core allows a quenching of the fluorescence intrinsic to the corresponding aminated or hydroxylated aromatic core. The remaining part of the quencher group qu. (that is to say the groups designated in formulas I" and II", by R$^1$, Pept., Glyc., R$^2$, R$^{2'}$, and R$_a$ to R$_e$) is cautiously chosen not to physically obscure the bond targeted by the enzyme activity to detect, and therefore to let this targeted bond accessible to the appropriate enzyme activity(ies). The ability of said remaining part of the quenching group qu. not to physically obscure the targeted bond is, essentially or exclusively, linked to the steric hindrance in the region of said targeted bond. In practice, said remaining part of the quenching group qu. should not be too cumbersome and/or should not develop steric interactions with said targeted bond.

In the context of the present invention, R$^1$, Pept., Glyc., R$^2$, R$^{2'}$, and R$_a$ to R$_e$ can be advantageously chosen for their intrinsic properties, particularly their hydrophilic/hydrophobic properties, for instance so as to modulate the properties of diffusibility of the resulting fluorogenic substrate, consistent with the medium wherein the latter will/would be implemented in (e.g. a liquid, solid or semisolid reaction medium).

Advantageously and according to the invention, the choice of Pept., Glyc., R$^2$ and R$^{2'}$ also depends on the targeted enzymes. Pept., Glyc., R$^2$ and R$^{2'}$ are therefore advantageously designed so as to mimic natural substrates of the targeted enzymes; more particularly, they comprises patterns that are recognized by the targeted enzymes.

The general principle of detection of an enzymatic activity according to the invention, using a fluorogenic/fluorescent probe of the invention, is summarized in Scheme 1. For each fluorogenic substrate to be used, the appropriate quencher group qu. (more particularly, its linkage with the aromatic core) is chosen in accordance with the specific enzyme activity to detect.

Scheme 1: Fluorescence detection of an enzyme activity according to the invention

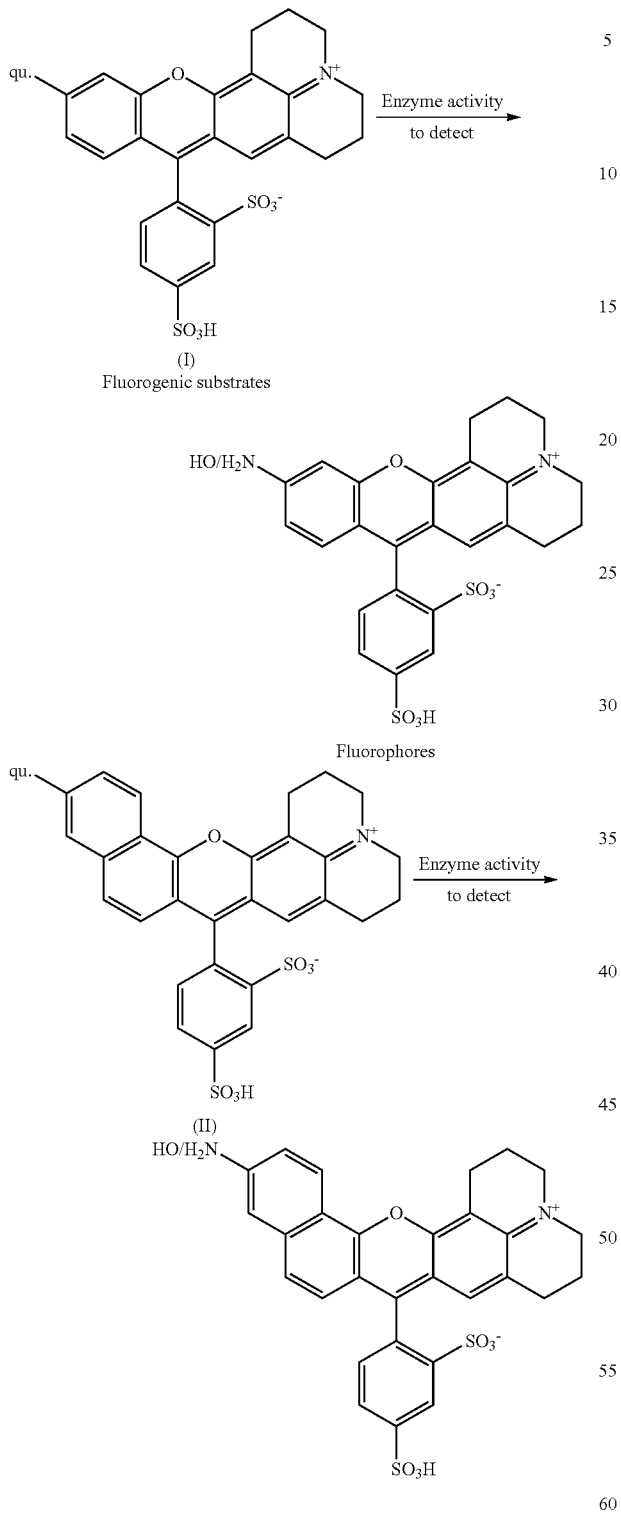

(I)
Fluorogenic substrates (II)

Fluorophores

For optimized performances of the fluorogenic/fluorescent probes according to the invention, it is advised to use the latter with a control of the medium pH regarding the pKa of the fluorophores.

According to a first preferred embodiment and as schematically and partially illustrated by Scheme 2, the present invention concerns a method of detecting a nitroreductase activity, as well as a method of detecting/identifying microorganisms expressing a nitroreductase activity, wherein at least one fluorogenic substrate of formula I or II, with qu. designating a —$NO_2$ group, as previously defined, is used.

In this regard, by "nitroreductase activity", it is understood any enzyme activity that is capable of catalyzing, partially or entirely, the chemical reaction schematically represented in Scheme 2, that is to say any enzyme activity that is capable to convert a fluorogenic nitro-substrate of the invention into an amino fluorophore of the invention (namely SR101-110 or SR101-NaphtNH$_2$) or into the following intermediary forms:

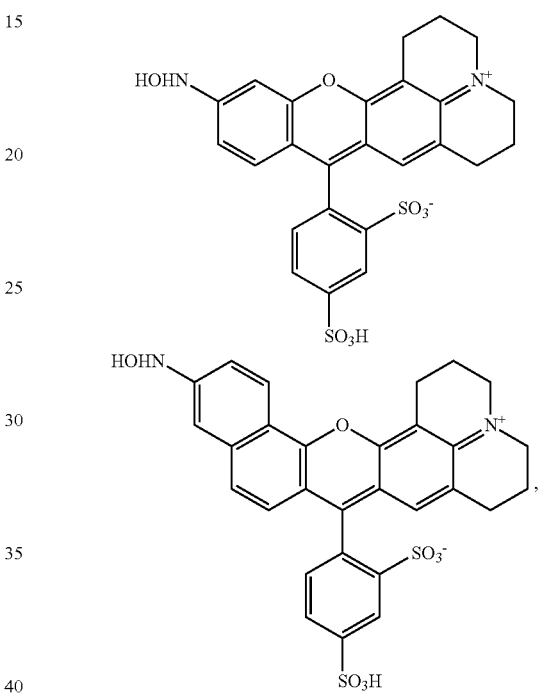

the reduction of these hydroxylamino products into an amino fluorophore of the invention (namely SR101-110 or SR101-NaphtNH$_2$) can further involve either an enzymatic or a chemical reaction.

Scheme 2: Fluorescence detection of a nitroreductase activity according to the invention

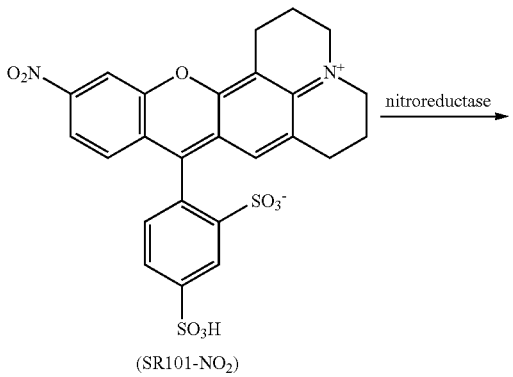

(SR101-NO$_2$)

: Formula I with qu. = —NO$_2$ (Formula I″ with Z = —NO$_2$)

-continued

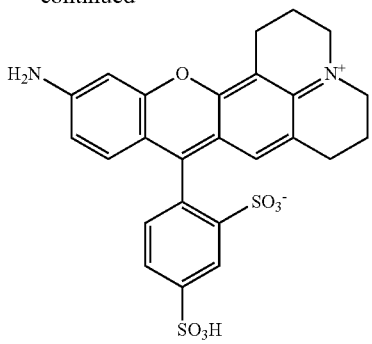

(SR101-110)

: Formula I' comprising —NH$_2$ (Formula I" with Z = —NH$_2$)

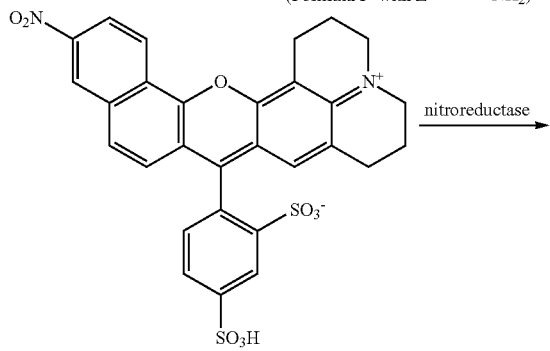

(SR101-NaphtNO$_2$)

: Formula II with qu. = —NO$_2$ (Formula II" with Z = —NO$_2$)

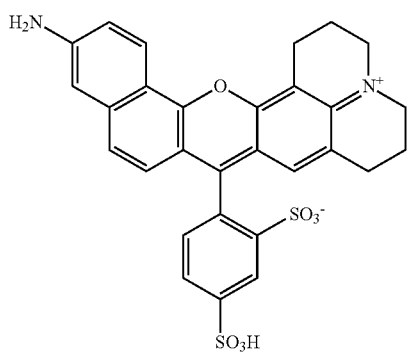

(SR101-NaphtNH$_2$)

: Formula II' comprising —NH$_2$ (Formula II" with Z = —NH$_2$)

It is also convenient to note that the previously mentioned hydroxylamino products are also fluorescent compounds. Therefore, the nitro fluorogenic substrates of the invention have the advantage to produce a fluorescence even in the first stage of the nitroreduction reaction.

To operate, some enzymes involved in a nitroreduction activity need flavin such as flavin mononucleotide (FMN), as a coenzyme, and/or NAD(P)H, as a cofactor. When a nitroreductase activity is searched in a biological sample, even if the latter can already comprise FMN and NADH and/or NADPH (for example, intrinsically provided by the tested microorganisms themselves), further to an appropriate fluorogenic substrate, an additional quantity of flavin (for example FMN), as well as a possible additional quantity of NADH and/or NADPH, are advantageously used.

According to a second preferred embodiment and as schematically and partially illustrated by Scheme 3, the present invention concerns a method of detecting an azoreductase activity, as well as a method of detecting/identifying microorganisms expressing an azoreductase activity, wherein at least one fluorogenic substrate of formula I or II, with qu. designating —N═N—R$^1$, is used; R$^1$ is any organic group that does not obscure the azo bond (that is directly linked to the aromatic core).

In this regard, by "azoreductase activity", it is understood any enzyme activity that is capable of catalyzing the chemical reaction schematically illustrated in below Scheme 3, that is to say an enzyme activity that is capable to convert a fluorogenic azo substrate of the invention into an amino fluorophore of the invention (namely SR101-110 or SR101-NaphtNH$_2$).

Scheme 3: Fluorescence detection of an azoreductase activity according to the invention

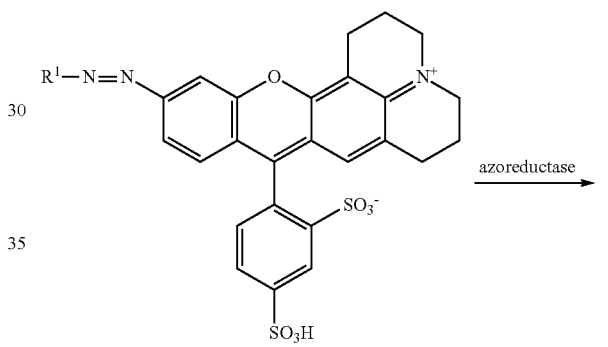

: Formula I with qu. = —N═N—R$^1$ (Formula I" with Z = —N═N—R$^1$)

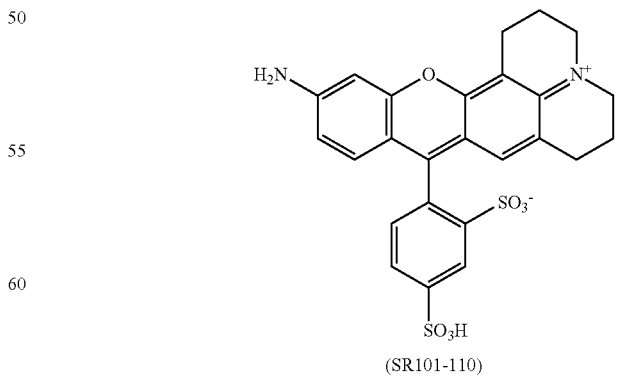

(SR101-110)

: Formula I' comprising —NH$_2$ (Formula I" with Z = —NH$_2$)

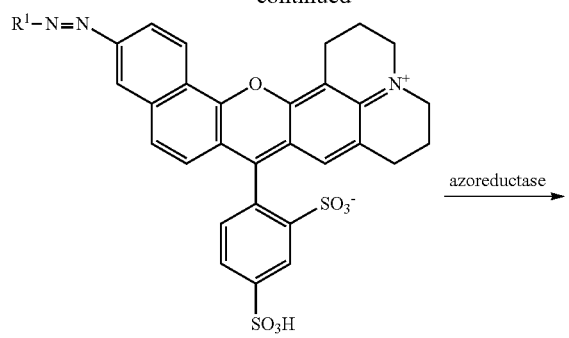

: Formula I with qu. = —N=N—R¹

(Formula I″ with Z = —N=N—R¹)

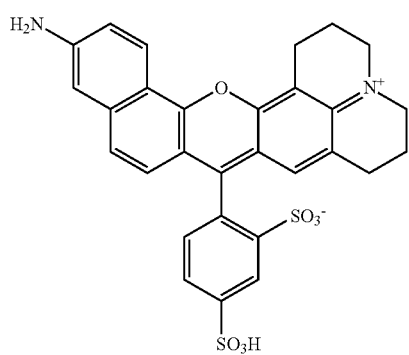

(SR101-NaphtNH₂)

: Formula II′ compromising —NH₂

(Formula II″ with Z = —NH₂)

Like nitroreductases, azoreductases are enzymes that need flavin, such as FMN, and NAD(P)H to operate. When an azoreductase activity is searched in a biological sample, even if the latter can already comprises FMN and NADH and/or NADPH (for example, intrinsically provided by the tested microorganisms themselves), further to an appropriate fluorogenic substrate of the invention, an additional quantity of flavin (for example of FMN), as well as a possible additional quantity of NADH and/or NADPH, are advantageously used.

According to the invention, R¹ designates any organic group that does not obscure the corresponding azo bond. Advantageously, R¹ is an organic group having a main chain formed by 1 to 30 atoms, most of carbon atoms and possibly nitrogen, oxygen and/or sulfur atoms. Also, said main chain being possibly functionalized and/or branched with at least one organic side chain.

Advantageously and according to the same embodiment, said main chain and/or said at least one organic side chain, correspond to a $C_1$-$C_{20}$ hydrocarbon chain selected in the group consisting of: alkyl, alkenyl (mono- or poly-insaturated), aryl, cycloalkyl and/or cycloalkenyl (mono- or poly-insaturated).

Advantageously and according to the invention, R¹ is a branched and/or functionalized aryl, more preferably a branched and/or functionalized phenyl, and even more preferentially, it is chosen in the group consisting of:

4-(N-butanoate, N-methyl)anilinyl:

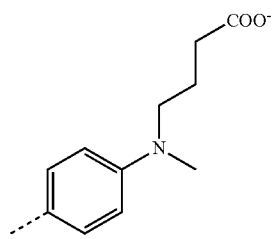

4-(N-azidoethyl, N-methyl)anilinyl:

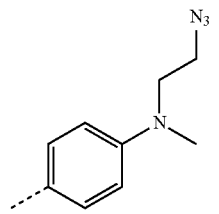

4-amino(N-methyl, N-ethylaniline)phenyl:

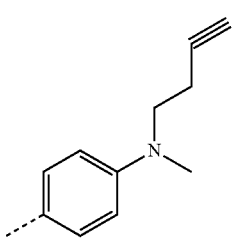

4-(N-3-maleimidylpropyl,N-methyl)anilinyl:

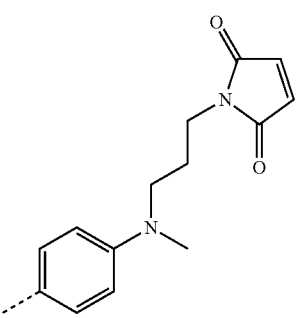

4-(N-3-aminopropyl,N-methyl)anilinyl:

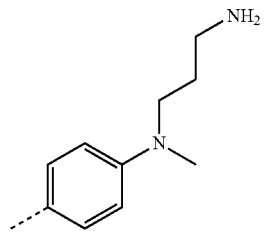

4-(N,N-dimethyl)anilinyl:

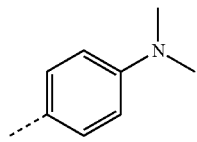

4-(N,N-di-3-azidoethyl)anilinyl:

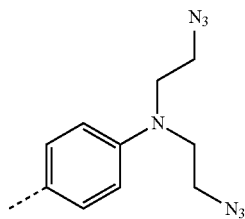

1,1'-((1,1'-((phenylazanediyl)bis(ethane-2,1-diyl))bis(1H-1,2,3-triazole-4,1-diyl))bis(methylene))bis(1-methylpyrrolidin-1-ium):

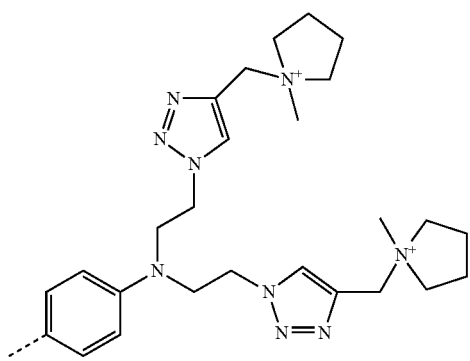

3,3'-(1,1'-((phenylazanediyl)bis(ethane-2,1-diyl))bis(1H-1,2,3-triazole-4,1-diyl)bis(methylene))bis(piperidine-1-ium-1,1-diyl)bis(propane-1-sulfonate):

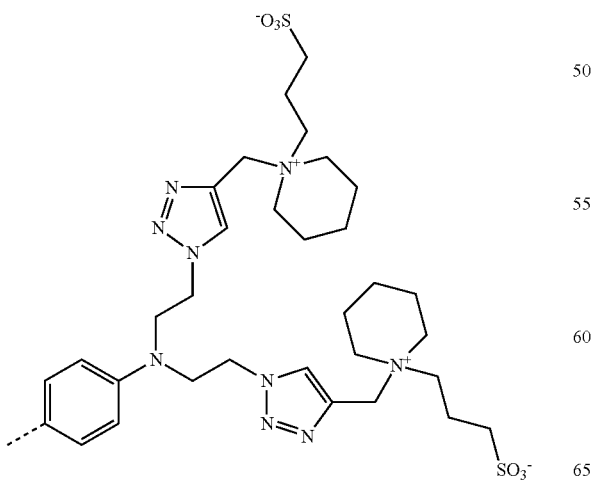

According to a third preferred embodiment and as schematically and partially illustrated by Scheme 4, the present invention concerns a method of detecting a peptidase activity, as well as a method of detecting/identifying microorganisms expressing a peptidase activity, wherein at least one fluorogenic substrate of formula I or II, with qu. designating —NHCO-Pept., is used; Pept. is any peptide residue or any organic group that does not obscure the amide bond that is directly linked to the aromatic core.

In this regard, by "peptidase activity", it is understood any enzyme activity that is capable of catalyzing the chemical reaction schematically illustrated in below Scheme 4, that is to say any enzyme activity that is capable to convert a fluorogenic peptide substrate of the invention into an amino fluorophore of the invention (namely SR101-110 or SR101-NaphtNH$_2$).

Scheme 4: Fluorescence detection of a peptidase activity according to the invention

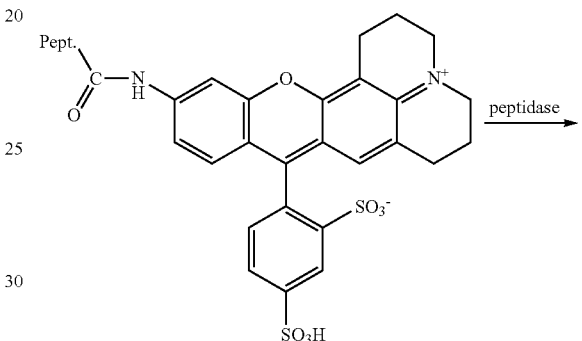

: Formula I with qu. = —NHCO-Pept.
(Formula I″ with Z = —NHCO-Pept.)

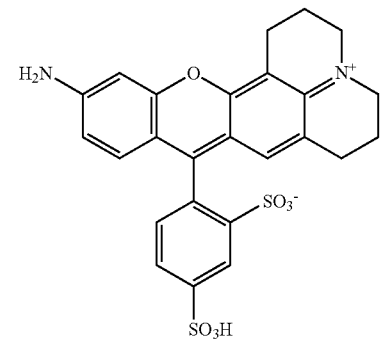

(SR101-110)
: Formula I′ with —NH$_2$
(Formula I″ with Z = —NH$_2$)

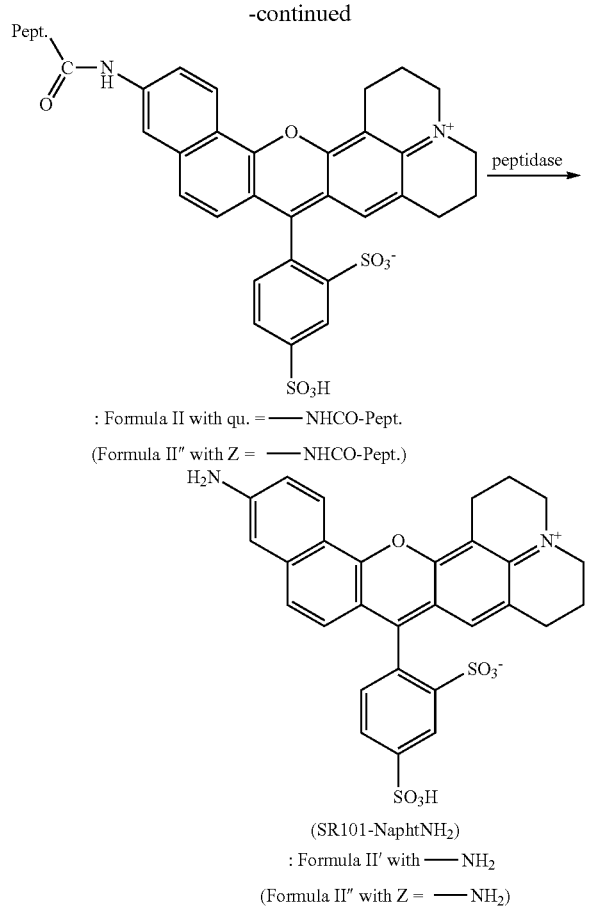

: Formula II with qu. = ──NHCO-Pept.
(Formula II″ with Z = ──NHCO-Pept.)

(SR101-NaphtNH₂)
: Formula II′ with ──NH₂
(Formula II″ with Z = ──NH₂)

In addition, "peptide residue" is understood to mean an oligopeptide chain comprising from 1 to 10 amino acid residues, the C-terminus amino acid residue of which forms an amide bond with the aromatic core.

Said oligopeptide chain may possibly comprise a blocking agent at its N-terminus end. By way of example, mention may be made of t-butoxycarbonyl (Boc), 9-fluorenylmethyloxycarbonyl (Fmoc), a solubilizing agent such as succinoyl (HO₂C—(CH₂)₂—CO), or else a non-metabolizable amino acid, i.e. an unnatural amino acid, such as pipecolic acid, isonipecotic acid or the D form of an amino acid, such as D-phenylalanine, alpha-sulfo-beta-alanine and 4-amino-2-sulfobutyric acid.

Advantageously and according to this third embodiment, Pept. is designed so as to mimic a natural substrate of a targeted peptidase; particularly, it comprises peptidic patterns recognized by a specific peptidase (see for examples, Orenga et al., J. Microbiol. Meth., 2009, 79: 139-155;and Rawlings et al., Nucleic Acids Res., 2014, 42).

According to this particular preferred embodiment, Pept. is an oligopeptide residue comprising 1 to 6 amino acid residues. Even more preferentially, Pept. is chosen in the group consisting of: L-alanyl, L-glycyl, pyro-glutamyl, beta-alanyl, L-prolyl, Boc-Val-Pro-Arg, Ala-Ala-Ala.

According to a fourth preferred embodiment and as schematically and partially illustrated by Scheme 5, the present invention concerns a method of detecting a glycosidase activity, as well as a method of detecting/identifying microorganisms expressing a glycosidase activity, wherein at least one fluorogenic substrate of formula I or II, with qu. designating —O-Glyc., is used; Glyc. is an oligoglycoside residue that does not obscure the glycosidic bond that is directly linked to the aromatic core.

In this regard, by "glycosidase activity", it is understood any enzyme activity that is capable of catalyzing the chemical reaction schematically illustrated in below Scheme 5, that is to say any enzyme activity that is capable to convert a fluorogenic glycosyl substrate of the invention into a hydroxylated fluorophore of the invention (namely SR101-OH or SR101-NaphtOH).

Scheme 5: Fluorescence detection of a glycosidase activity according to the invention

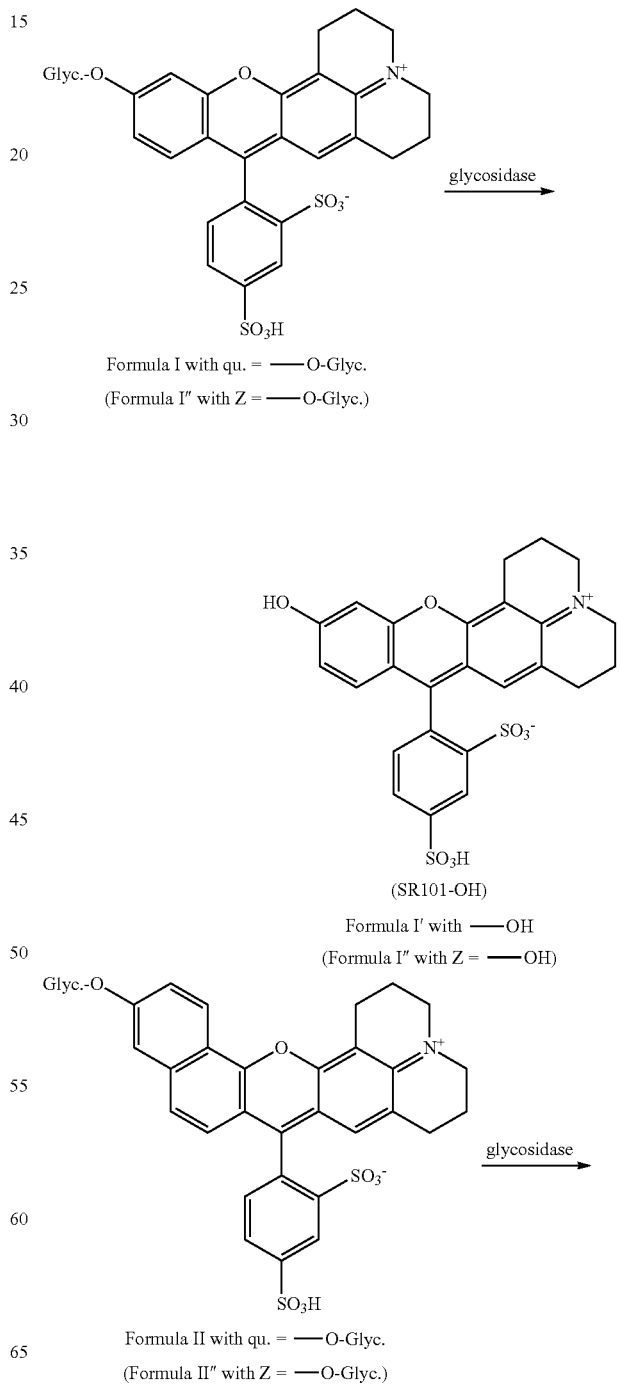

Formula I with qu. = ──O-Glyc.
(Formula I″ with Z = ──O-Glyc.)

(SR101-OH)
Formula I′ with ──OH
(Formula I″ with Z = ──OH)

Formula II with qu. = ──O-Glyc.
(Formula II″ with Z = ──O-Glyc.)

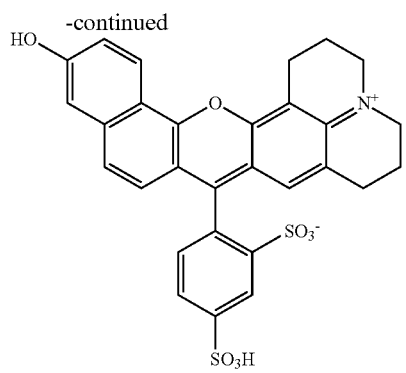

(SR101-NaphtOH)

Formula II′ with —OH (Formula II″ with Z = —OH)

Furthermore, "oligoglycoside residue" is understood to mean a residue of monoglycoside or polyglycoside (homo- or hetero-polyglycoside). More particularly, an olicoglycoside residue according to the invention comprises preferentially 1 to 5 glycosidic units, each glycosidic unit being chosen in the group consisting of: glucosyl, galactosyl, mannosyl, fructosyl, glucuronyl, hexosaminyl, arabinosyl, fucosyl, xylosyl and ribosyl.

Advantageously and according to the invention, Glyc. is chosen in the group consisting of residues of: glucoside, arabinoside, fucoside, xyloside, cellobioside, galactoside, mannoside, glucuronide, hexosaminide, chitoside, maltoside and riboside.

In accordance with the targeted glycosidase, a person skilled in the art is perfectly able to choose the appropriate fluorogenic substrate of the invention, with the appropriate Glyc.

Advantageously and according to the invention, said glycosidase activity is chosen in the group consisting of: glucosidase, amylase, arabinosidase, fucosidase, xylosidase, cellobiosidase, galactosidase, mannosidase, glucuronidase, hexosaminidase, chitobiosidase, maltosidase and ribosidase.

According to a fifth preferred embodiment as schematically and partially illustrated by Schemes 6a to 6c, the present invention concerns a method of detecting an esterase activity—more specifically a carboxylic esterase (or carboxylesterase) activity, a phosphatase (or phosphate esterase or phosphoesterase) activity or a sulfatase (or sulfate esterase, or sulfoesterase) activity—, as well as a method of detecting/identifying microorganisms expressing an esterase activity, wherein it is used at least one fluorogenic substrate of formula I or II, as previously defined and wherein qu. is chosen in the group consisting of: —O—C(O)—$R^2$, —O—P(O)(O$R^2$)(O$R^{2\prime}$) and —O—S(O)$_2$—$R^2$; $R^2$ and $R^{2\prime}$ being a hydrogen atom or any organic group that does not obscure the ester bond.

When they do not designate a hydrogen atom, $R^2$ and $R^{2\prime}$ are organic groups with a main chain formed by 1 to 30 atoms, most of carbon atoms and possibly nitrogen, oxygen and/or sulfur atoms. Also, said main chain being possibly functionalized and/or branched with at least one organic side chain. Preferentially, said main chain and/or said at least one organic side chain, correspond to a $C_1$-$C_{20}$ hydrocarbon chain selected in the group consisting of: alkyl, alkenyl (mono- or poly-insaturated), aryl, cycloalkyl and/or cycloalkenyl (mono- or poly-insaturated).

Advantageously and according to a particular embodiment, $R^2$ and $R^{2\prime}$ is independently chosen in the group consisting of: hydrogen atom, methyl, ethyl, propyl, isopropyl, butyl, t-butyl, phenyl and benzyl.

More particularly, by "carboxylesterase activity" (or carboxylic-ester hydrolase), it is understood any enzyme activity that is capable of catalyzing the chemical reaction schematically represented in below Scheme 6a, that is to say any enzyme activity that is capable to convert fluorogenic carboxyester of the invention into a hydroxylated fluorophore of the invention (namely SR101-OH or SR101-NaphtOH).

Scheme 6a: Fluorescence detection of a carboxylesterase activity according to the invention

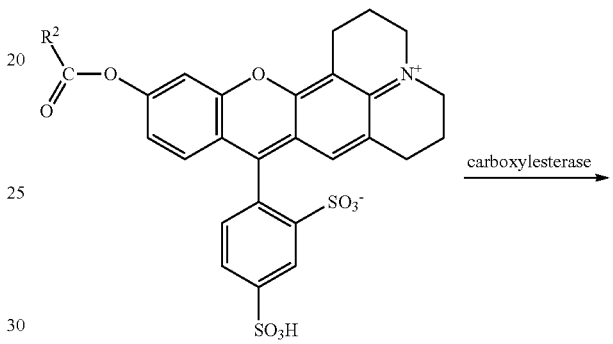

Formula I with qu. = —O—C(O)—$R^4$ (Formula I″ with Z = —O—C(O)—$R^4$)

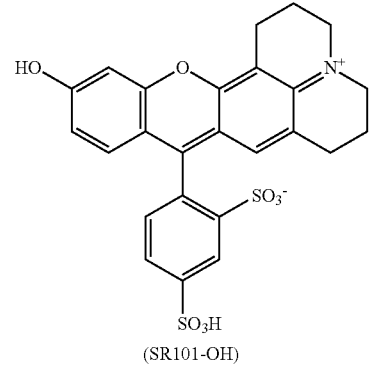

(SR101-OH)

Formula I′ with = —OH (Formula I″ with Z = —OH)

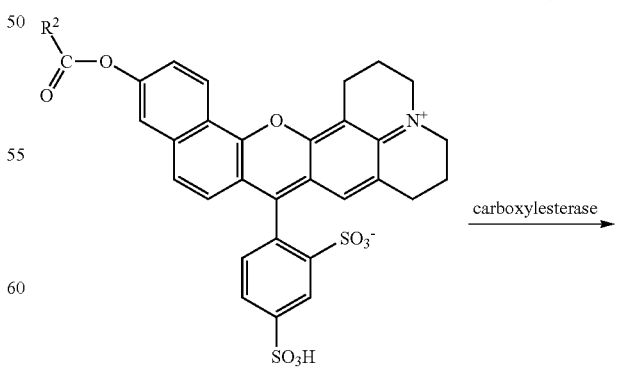

Formula I with qu. = —O—C(O)—$R^4$ (Formula I″ with Z = —O—C(O)—$R^4$)

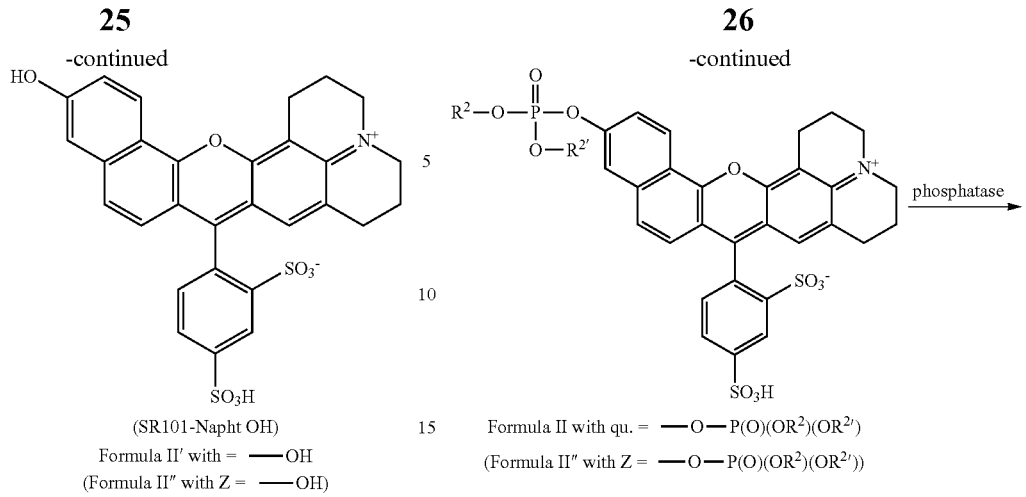

(SR101-Napht OH)
Formula II' with = ──OH
(Formula II" with Z = ──OH)

Formula II with qu. = ──O──P(O)(OR$^2$)(OR$^{2'}$)
(Formula II" with Z = ──O──P(O)(OR$^2$)(OR$^{2'}$))

Besides, by "phosphatase activity", it is understood any enzyme activity that is capable of catalyzing the dephosphorylation reaction schematically illustrated in below Scheme 6b, that is to say any enzyme activity that is capable to convert an appropriate fluorogenic phosphoester (phosphomonoester or phosphodiester) of the invention into a hydroxylated fluorophore of the invention (namely SR101-OH or SR101-NaphtOH).

Scheme 6b: Fluorescence detection of a phosphatase activity according to the invention

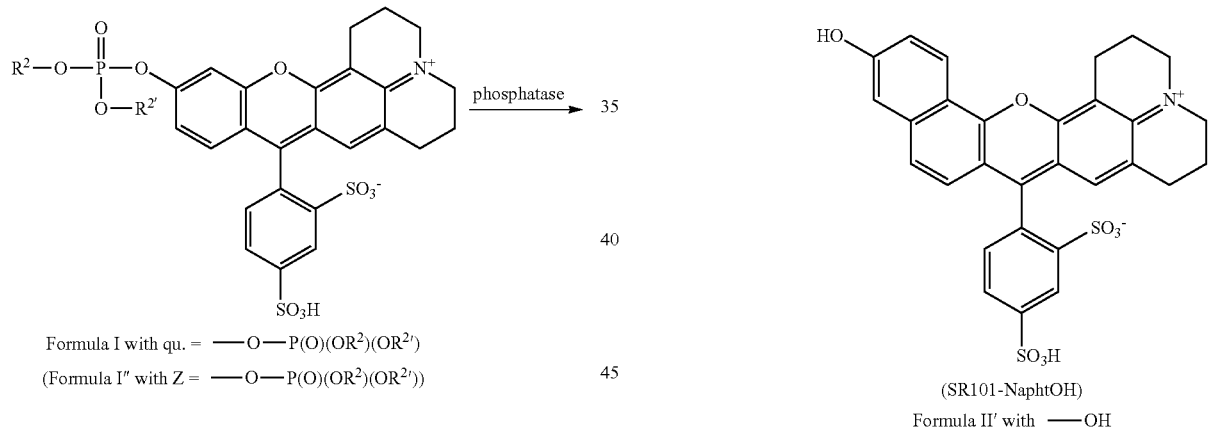

Formula I with qu. = ──O──P(O)(OR$^2$)(OR$^{2'}$)
(Formula I" with Z = ──O──P(O)(OR$^2$)(OR$^{2'}$))

(SR101-NaphtOH)
Formula II' with ──OH
(Formula II" with Z = ──OH)

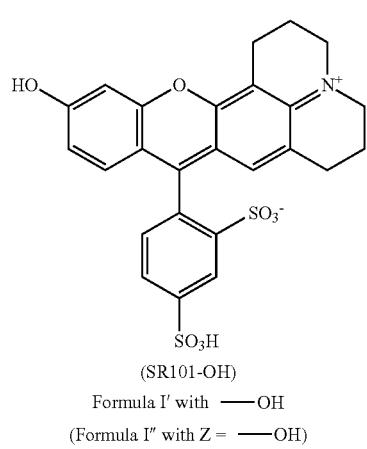

(SR101-OH)
Formula I' with ──OH
(Formula I" with Z = ──OH)

It is convenient to note that phospholipases C (PLC) refer to a particular class of phosphatases that, in physiological conditions, are involved in the cleavage of phospholipids (such as, for instance, phosphatidylinositol-4,5-bisphosphate, 5-bromo-4-chloro-3-indoxyl myo-inositol-1-phosphate, ammonium salt, 5-bromo-4-chloro-3-indoxyl choline phosphate).

The fluorogenic phosphoesters of the invention can be prepared and used as fluorogenic substrates for detecting a large variety of phosphoesterase activities, including a phospholipase C activity.

Additionally, in the sense of the present invention, by "sulfatase activity", it is understood any enzyme activity that is capable of catalyzing the reaction schematically represented in below scheme 6c, that is to say an enzyme activity that is capable to convert an appropriate fluorogenic sulfate ester of the invention into a hydroxylated fluorophore of the invention (namely SR101-OH or SR101-NaphtOH).

Scheme 6c: Fluorescence detection of a sulfatase activity according to the invention

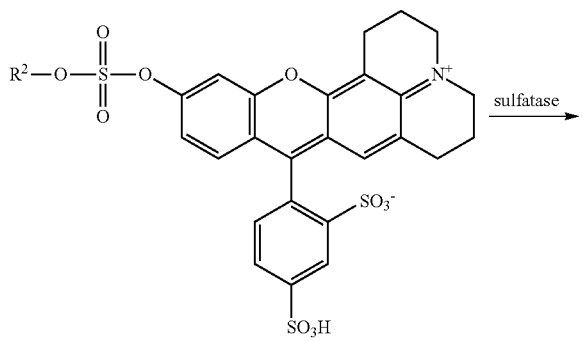

Formula I with qu. = —O—S(O)$_2$—OR$^3$
(Formula I″ with Z = —O—S(O)$_2$—OR$^3$)

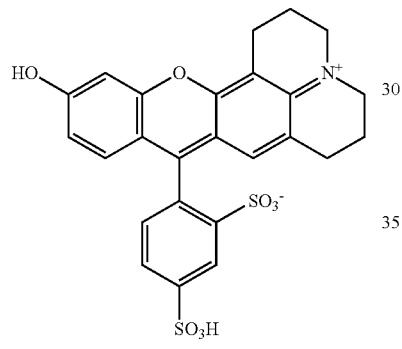

(SR101-OH)
Formula I′ with —OH
(Formula I″ with Z = —OH)

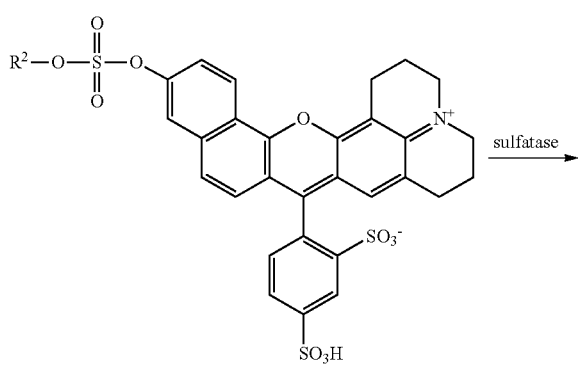

Formula II with qu. = —O—S(O)$_2$—OR$^3$
(Formula II″ with Z = —O—S(O)$_2$—OR$^3$)

-continued

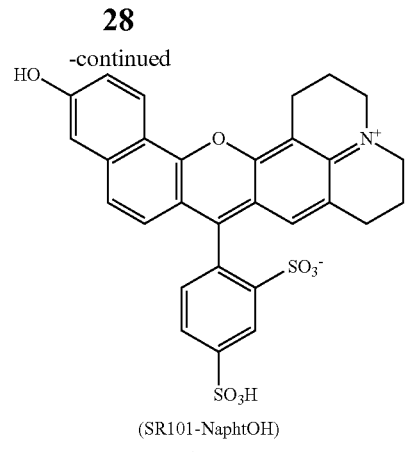

(SR101-NaphtOH)
Formula II′ with —OH
(Formula II″ with Z = —OH)

According to a sixth preferred embodiment and as schematically and partially illustrated by Scheme 7, the present invention concerns a method of detecting a myeloperoxidase activity, as well as a method of detecting/identifying microorganisms expressing a myeloperoxidase activity, wherein at least one fluorogenic substrate of formula I or II, with qu. designating:

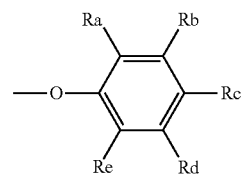

is used; $R_a$, $R_b$, $R_c$, $R_d$ and $R_e$ being a hydrogen atom or any organic group that does not obscure the arylether bond that is directly linked to the aromatic core.

In this regard, by "myeloperoxidase activity", it is understood any enzyme activity that is capable of catalyzing the chemical reaction schematically illustrated in below Scheme 7, that is to say any enzyme activity that is capable to convert a fluorogenic arylether substrate of the invention into an hydroxylated fluorophore of the invention (namely SR101-OH or SR101-NaphtOH).

Scheme 7: Fluorescence detection of a myeloperoxidase activity according to the invention

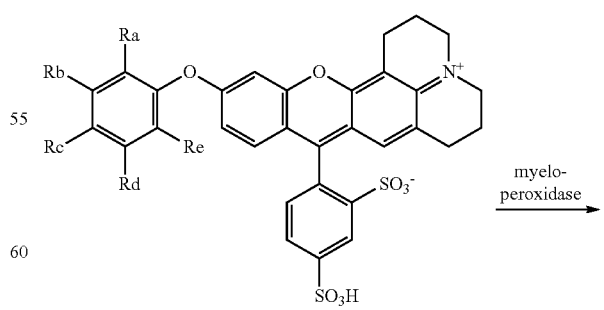

: Formula I with qu. = a phenyloxy or a derivative
(Formula I″ with Z = a phenyloxy or a derivative)

-continued

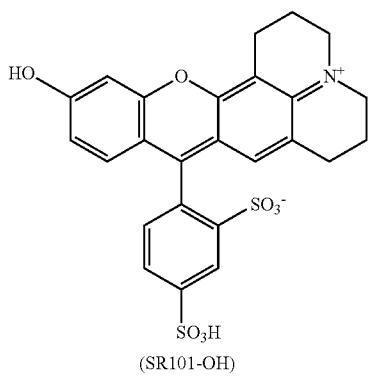

(SR101-OH)

: Formula I' with ——NH$_2$ (Formula I" with Z = ——NH$_2$)

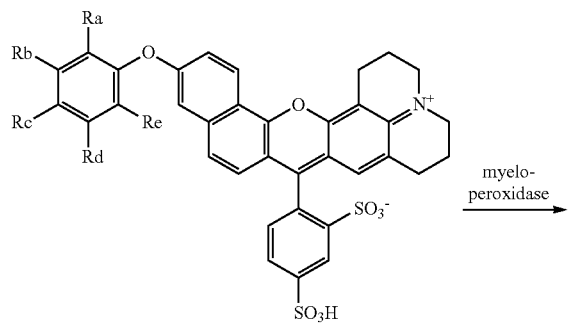

: Formula II with qu. = a phenyloxy or a derivative (Formula II" with Z = a phenyloxy or a derivative)

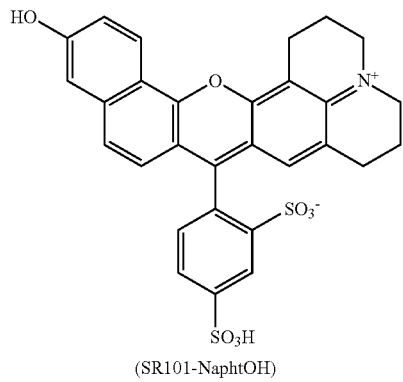

(SR101-NaphtOH)

: Formula II' with ——NH$_2$ (Formula II" with Z = ——NH$_2$)

Advantageously and according to this sixth embodiment, one of any $R_a$, $R_b$, $R_c$, $R_d$ and $R_e$ is —NO$_2$ or —NH$_2$, and the others hydrogen atoms. More preferentially, $R_c$ is —NO$_2$ or —NH$_2$, and $R_a$, $R_b$, $R_d$ and $R_e$ are hydrogen atoms.

The invention is also directed to a reaction medium allowing to carry out a method of detecting a particular enzyme activity, in microorganisms, according to the invention. Said reaction medium, notably useful for the detectionand/or identification of microorganisms, comprises at least one fluorogenic substrate of formula (I) or (II), as previously disclosed.

For better performances, said reaction medium may also comprise a quantity of NADH and/or NADPH, and possibly a quantity of flavin (for example FMN).

The invention also relates to a fluorogenic substrate and/or a fluorescent reporter molecule of the invention, a use of said compounds as probes for the detection of an enzyme activity, a method of detecting in microorganisms an enzyme activity, and a reaction medium (for example, useful for the detection and/or identification of microorganisms) which comprises a fluorogenic substrate of the invention, characterized in combination by all or some of the features mentioned above or below.

BRIEF DESCRIPTION OF THE DRAWINGS

Further features, objects and advantages of the invention will appear from reading the following description which presents by way of non-limiting examples an embodiment of the invention, with reference to the accompanying drawings, in which.

EXAMPLES

Example 1

Synthesis of Compounds of the Invention

Figure 1A:
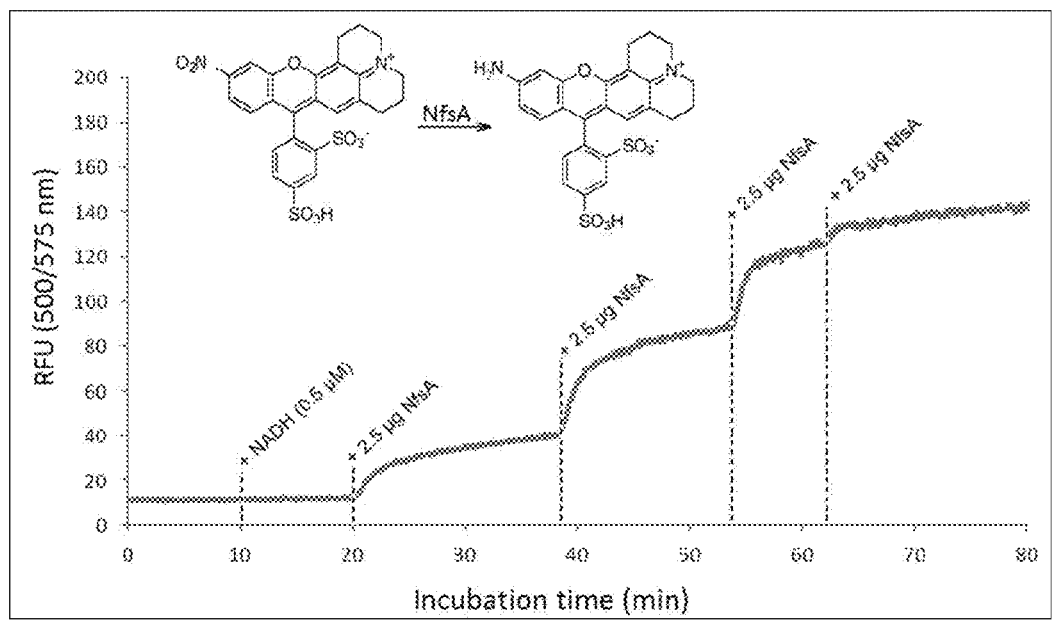
FIGS. 1a, 5a, 5b, 6 and 7 are graphics showing the appearance of a fluorescence and the enhancement of its intensity indicating the conversion of fluorogenic substrates of the invention (respectively SR101-NO$_2$, SR101-NaphtOAc, SR101-NaphtO-lauric acid, SR101-NaphtO(SO$_3$H) and SR101-NaphtO(para-aminophenyl)) into fluorophores of the invention, under the action of an appropriate catalytic activity (namely a nitroreductase, an ethanoate esterase, and a sulfatase activities, as well as a chemical simulated myeloperoxidase activity)

A) Synthesis of the Four Fluorescent Compounds of the Invention

The four fluorescent compounds of the invention can be synthesized according to the following general procedure.

Scheme 8: Synthesis of the fluorescent compounds of the invention

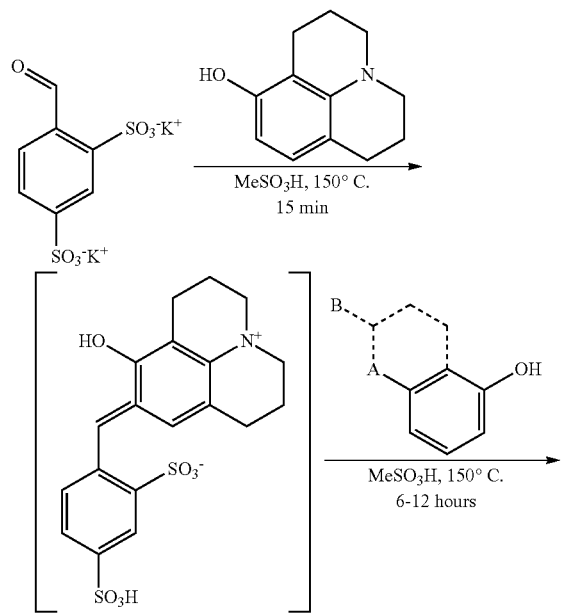

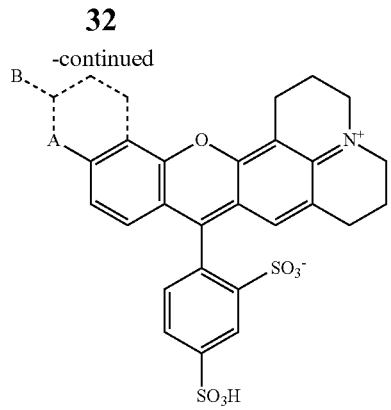

A mixture of 8-hydroxyjulolidine (1 equiv.) and 4-formylbenzene-1,3-disulfonic acid, dipotassium salt (1 equiv.) are dissolved in methanesulfonic acid and the mixture is heated at 150° C. for 15 min, using a sealed tube. Thereafter, upon cooling to room temperature, the phenolic reaction partner (1 equiv.) is added and the mixture is stirred at 150° C. The reaction is checked for completion by RP-HPLC, diluted with ultrapure water and finally purified by semi-preparative RP-HPLC. The product-containing fractions is lyophilized to give the targeted fluorescent compound as a TFA salt.

In following Table 2 are provided further details of the implementation of this synthetic procedure, regarding the preparation of the four distinct fluorescent sulfoxanthene derivatives of the invention.

TABLE 2

Synthesis of the fluorescent compounds of the invention

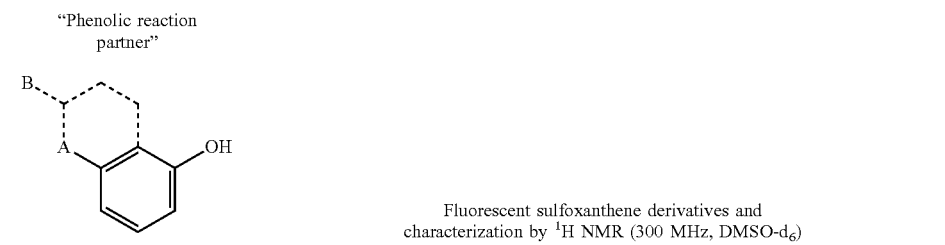

| "Phenolic reaction partner" | Fluorescent sulfoxanthene derivatives and characterization by $^1$H NMR (300 MHz, DMSO-$d_6$) |
|---|---|
| 3-aminophenol 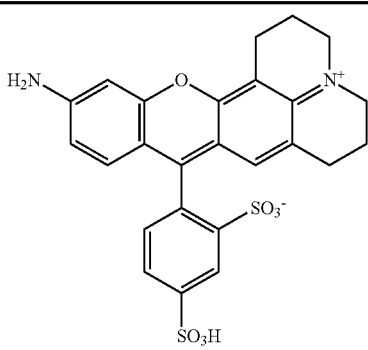 | $^1$H NMR: δ = 1.73 (bs, 4H), 2.35 (bs, 4H), 3.32 (bs, 4H), 6.31 (s, 1H), 6.40 (d, $^3$J(H—H) = 9.5 Hz, 1H), 6.50 (bs, 1H), 6.70 (d, $^3$J(H—H) = 9.1 Hz, 1H), 7.09 (d, $^3$J(H—H) = 7.8 Hz, 1H), 7.96 (d, $^3$J(H—H) = 7.8 Hz), 8.40 (bs, 1H) ppm. HRMS (ESI−) calcd for [M − H]$^−$ $C_{25}H_{22}N_2O_7S_2^-$ 525.0796, found 525.0787 |

SR101-110

TABLE 2-continued

Synthesis of the fluorescent compounds of the invention

"Phenolic reaction partner"

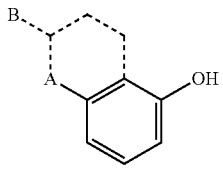

Fluorescent sulfoxanthene derivatives and characterization by $^1$H NMR (300 MHz, DMSO-$d_6$)

| 1,3-dihydroxybenzene | 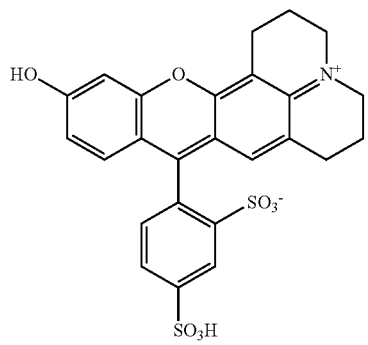<br>SR101-OH | $^1$H NMR: δ = 1.73 (bs, 4H), 2.35 (bs, 4H), 3.32 (bs, 4H), 6.31 (s, 1H), 6.40 (d, $^3$J(H—H) = 9.5 Hz, 1H), 6.50 (bs, 1H), 6.70 (d, $^3$J(H—H) = 9.1 Hz, 1H), 7.09 (d, $^3$J(H—H) = 7.8 Hz, 1H), 7.96 (d, $^3$J(H—H) = 7.8 Hz), 8.40 (bs, 1H) ppm. HRMS (ESI−) calcd for [M − H]$^−$ $C_{25}H_{21}NO_8S_2^−$ 526.0636, found 526.0635. |
|---|---|---|
| 1,6-dihydroxy-naphthalene | 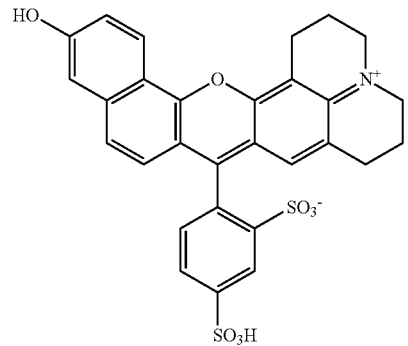 | $^1$H NMR: δ = 1.90 (bs, 2H), 2.05 (bs, 2H), 2.73 (bs, 2H), 3.06 (bs, 2H), 3.62 (bs, 4H), 6.85 (s, 1H), 6.94 (d, $^3$J(H—H) = 8.6 Hz, 1H), 7.20 (d, $^3$J (H—H) = 7.3 Hz, 1H), 7.26 (s, 1H), 7.32 (d, $^3$J (H—H) = 8.8 Hz, 1H), 7.58 (d, $^3$J (H—H) = 9.0 Hz, 1H), 7.78 (d, $^3$J (H—H) = 7.3 Hz, 1H), 8.29 (s, 1H), 8.52 (d, $^3$J(H—H) = 8.8 Hz, 1H) ppm. HRMS (ESI−) calcd for [M − H]$^−$ $C_{29}H_{23}NO_8S_2^−$ 576.0792, found 576.0803 |

TABLE 2-continued

Synthesis of the fluorescent compounds of the invention

"Phenolic reaction partner"

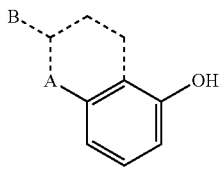

Fluorescent sulfoxanthene derivatives and characterization by $^1$H NMR (300 MHz, DMSO-$d_6$)

| | SR101-NaphtOH | |
|---|---|---|
| 6-aminonaphthol | 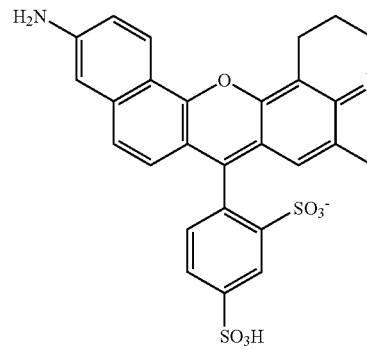 | $^1$H NMR: δ = 1.91 (bs, 2H), 2.10 (bs, 2H), 2.73 (bs, 2H), 3.18 (bs, 2H), 3.66 (bs, 4H), 6.89 (s, 1H), 6.96 (d, $^3$J(H—H) = 8.6 Hz, 1H), 7.19 (d, $^3$J(H—H) = 7.3 Hz, 1H), 7.31 (d, $^4$J(H—H) = 2.3 Hz, 1H), 7.40 (dd, $^3$J(HH) = 9.0 Hz, $^4$J(H—H) = 2.3 Hz, 1H), 7.60 (d, $^3$J(H—H)) = 9.0 Hz, 1H), 7.76 (dd, $^3$J(H—H) = 7.8 Hz, $^4$J(H—H) = 1.7 Hz, 1H), 8.28 (d, $^4$J(H—H) = 1.7 Hz, 1H), 8.63 (d, $^3$J(H—H) = 9.0 Hz, 1H)ppm. HRMS (ESI-) calcd for [M − H]$^-$ $C_{29}H_{24}N_2O_7S_2^-$ 575.0952, found 575.0938 |
| | SR101-NaphtNH$_2$ | |

B) Synthesis of the Fluorogenic Substrates of the Invention

1. Synthesis of Fluorogenic Azoreductase Substrates of the Invention

Some fluorogenic azo substrates of the invention can be synthesized from the amino fluorophores of the invention (SR101-110; SR101-NaphtNH$_2$), by performing the following general procedure.

Scheme 9: Synthesis of fluorogenic azoreductase substrates of the invention

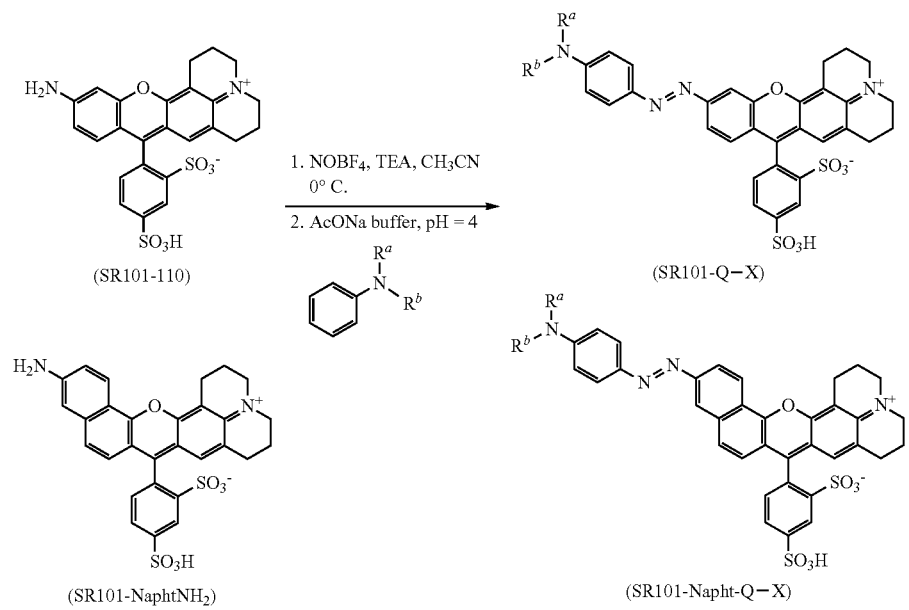

TFA salt of an amino fluorophore of the invention (1 equiv.) and TEA (1 equiv.) are dissolved in dry CH$_3$CN (0.38 mL) and the mixture is cooled to 0° C. and kept under an argon atmosphere. Then, solid NOBF$_4$ (1.5 equiv.) is added and the reaction mixture is stirred at 0° C. for 15 min.

Thereafter, AcONa buffer (0.1 M, pH=4.0) is added both to obtain a complete solubilization of the diazonium salt (or N-nitroso) intermediate and to quench excess NOBF$_4$. The functionalized tertiary aniline (1.1 equiv.) is dissolved in CH$_3$CN (0.1 mL) and this solution is added dropwise to the preformed diazonium salt intermediate. The reaction mixture is stirred at room temperature for 30 min.

Thereafter, the crude mixture is diluted with aqueous 0.1% TFA and purified by semi-preparative RP-HPLC. The product-containing fractions are lyophilized to give the TFA salt of the targeted fluorogenic azo substrate.

In following Table 3 are provided further details of the implementation of the previous synthetic method, regarding the preparation of specific examples of fluorogenic azoreductase substrates according to the invention.

TABLE 3

Examples of fluorogenic azoreductase substrates of the invention

Azoreductase substrates and characterization by $^1$H NMR (300 MHz, DMSO-d$_6$)

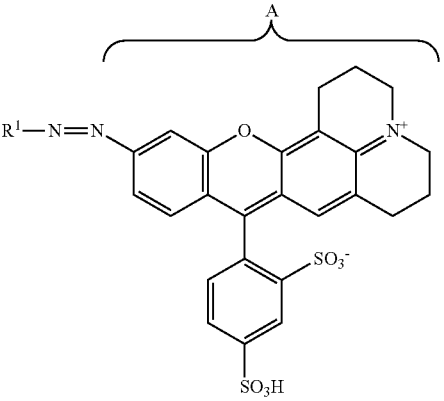

| Tertiary aniline | A | $^1$H NMR |
|---|---|---|
| 4-(Methyl(phenyl)amino)butanoic acid | SR101-Q-CO$_2$H | $^1$H NMR: δ = 1.80 (q, J = 6.9 Hz 2H), 1.87 (bs, 2H), 2.06 (bs, 2H), 2.31 (t, J = 6.9 Hz, 2H), 2.70 (bs, 2H), 3.02 (q, J = 7.2 Hz, 2H), 3.09 (s, 3H), 3.52 (t, J = 6.9 Hz, 2H), 3.68 (bs, 4H), 6.81 (s, 1H), 6.92 (d, J = 9.2 Hz, 2H), 7.22 (d, J = 4.9 Hz, 1H), 7.25 (d, J = 4.1 Hz, 1H), 7.75 (dd, $^3$J = 8.7 Hz, 4J = 1.7 Hz, 1H), 7.78 (dd, $^3$J = 7.8 Hz, $^4$J = 1.5 Hz, 1H), 7.85 (d, J = 9.2 Hz, 2H), 7.96 (d, J = 1.7 Hz, 1H), 8.27 (d, J = 1.5 Hz, 1H). HRMS (ESI−) calcd for [M − H]$^-$ C$_{36}$H$_{32}$N$_4$O$_9$S$_2^+$ 729.1689, found 729.1680. |
| N-(2-Azidoethyl)-N-methylaniline | SR101-Q-N$_3$ | $^1$H NMR: δ = 1.89 (bs, 2H), 2.07 (bs, 2H), 2.70 (bs, 2H), 3.02 (m 2H), 3.13 (s, 3H), 3.59 (t, J = 6.0 Hz, 2H), 3.5-4.0 (m, 6H, masked by H$_2$O signal), 6.84 (s, 1H), 6.95 (s, 1H), 6.99 (s, 1H), 7.22 (d, J = 4.7 Hz, 1H), 7.25 (d, J = 5.6 Hz, 1H), 7.75 (m, 1H), 7.78 (m, 1H), 7.87 (s, 1H), 7.9 (s, 1H), 8.02 (d, J = 1.8 Hz, 1H), 8.28 (d, J = 1.5 Hz, 1H). HRMS (ESI+) calcd for [M + H]$^+$ C$_{34}$H$_{32}$N$_7$O$_7$S$_2^+$ 714.1805, found 714.1838 |
| N-methyl-N-(pent-4-ynyl)aniline | SR101-Q-CCH | $^1$H NMR: δ = 1.89 (bs, 2H), 2.07 (bs, 2H), 2.70 (bs, 2H), 3.02 (m 2H), 3.13 (s, 3H), 3.59 (t, J = 6.0 Hz, 2H), 3.5-4.0 (m, 6H, masked by H$_2$O signal), 6.84 (s, 1H), 6.95 (s, 1H), 6.99 (s, 1H), 7.22 (d, J = 4.7 Hz, 1H), 7.25 (d, J = 5.6 Hz, 1H), 7.75 (m, 1H), 7.78 (m, 1H), 7.87 (s, 1H), 7.9 (s, 1H), 8.02 (d, J = 1.8 Hz, 1H), 8.28 (d, J = 1.5 Hz, 1H). HRMS (ESI+) calcd for [M + H]$^+$ C$_{37}$H$_{36}$N$_4$O$_7$S$_2^+$ 711.1947, found 711.1937 |

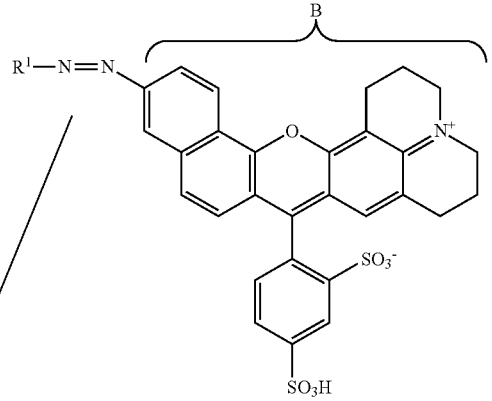

TABLE 3-continued

Examples of fluorogenic azoreductase substrates of the invention

Azoreductase substrates and characterization by $^1$H NMR (300 MHz, DMSO-$d_6$)

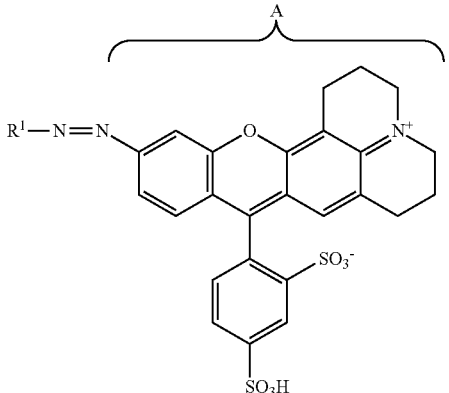

| Tertiary aniline | Structure | $^1$H NMR |
|---|---|---|
| 4-(N-3-maleimidylpropyl,N-methyl)anilinyl<br><br>SR101-Q-Mal | 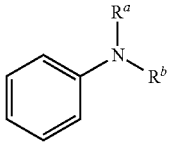 | $^1$H NMR: δ = 1.89 (bs, 4H), 2.07 (bs, 2H), 2.70 (bs, 2H), 3.02 (m 2H), 3.13 (s, 3H), 3.49 (t, J = 6.0 Hz, 2H), 3.7 (m, 6H, masked by H$_2$O signal), 6.84 (s, 1H), 6.95 (s, 1H), 6.99 (s, 1H), 7.22 (d, J = 4.7 Hz, 1H), 7.25 (d, J = 5.6 Hz, 1H), 7.75 (m, 1H), 7.78 (m, 1H), 7.87 (s, 1H), 7.9 (s, 1H), 8.02 (d, J = 1.8 Hz, 1H), 8.28 (d, J = 1.5 Hz, 1H). HRMS (ESI+) calcd for [M + H]$^+$ C$_{39}$H$_{36}$N$_5$O$_9$S$_2^+$ 782.1949, found 782.1981 |
| Boc-protected derivative of N-(3-aminopropyl)-N-methylaniline<br><br>SR101-Q-NH$_2$ | 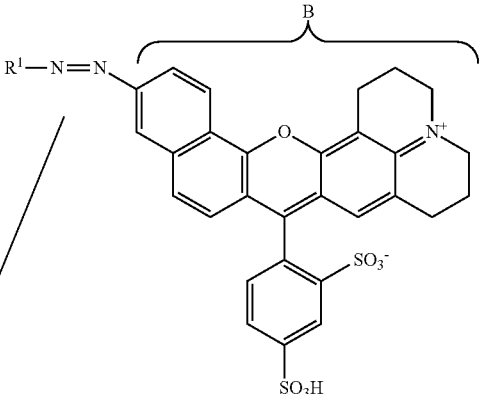 | $^1$H NMR: δ = 1.87 (bs, 4H), 2.05 (bs, 2H), 2.68 (bs, 2H), 2.86 (bs, 2H), 2.99 (bs, 2H), 3.08 (s, 3H), 3.5-3.7 (bs, 6H), 6.81 (s, 1H), 6.93 (d, J = 9.1 Hz, 2H), 7.25 (m, $^2$H), 7.70 (bs, 2H), 7.75-79 (m, 4H), 7.93 (bs, 1H), 8.28 (d, J = 1.5 Hz, 1H). HRMS (ESI+) calcd for [M + H]$^+$ C$_{35}$H$_{37}$N$_5$O$_7$S$_2^+$ 702.2056, found 702.2068 |
| N,N-dimethylaniline<br><br>SR101-NaphtNH$_2$-Hyp | 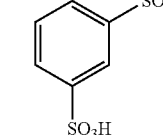 | $^1$H NMR: δ = 8.49 (d, $^3$J = 9.0 Hz, 1H), 8.31 (d, $^4$J = 1.6 Hz, 1H), 8.24 (s, 1H), 8.02 (d, $^3$J = 9.0 Hz, 1H), 7.94-7.81 (m, 2H), 7.78 (d, $^3$J = 9.0 Hz, 2H), 7.35 (d, $^3$J = 7.8 Hz, 1H), 7.05 (d, $^3$J = 8.9 Hz, 1H), 6.9-6.75 (m, 3H), 3.68 (m, 1H), 3.56 (m, 2H), 3.1 (q, $^3$J = 7.3 Hz, 6H, CH$_2$-TEA), 3.08 (s, 6H), 2.60 (m, 2H), 2.11 (m, 2H), 1.83 (m, 2H), 1.16 (t, $^3$J = 7.3 Hz, 9H, CH$_3$-TEA) ppm. LRMS (ESI−): calcd for C$_{37}$H$_{31}$N$_7$O$_7$S$_2^-$ 707.16 found: 707.27 |
| N,N-diazidoethyl-aniline<br><br>SR101-NaphtNH$_2$-Hyp-(N$_3$)$_2$ | 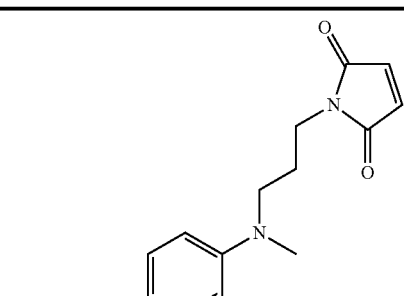 | $^1$H NMR: δ = 8.60 (d, $^3$J = 9.1 Hz, 1H), 8.32 (m, 2H), 8.10 (d, $^3$J = 9.1 Hz, 1H), 7.95-7.80 (m, 4H), 7.35 (d, $^3$J = 7.8 Hz, 1H), 7.10-6.95 (m, 3H), 6.84 (s, 1H) 3.9-3.5 (m, 12H), 3.2 (m, 2H), 3.06 (q, $^3$J = 7.3 Hz, 6H, CH$_2$-TEA), 2.62 (m, 2H), 2.15 (m, 2H), 1.83 (m, 2H), 1.16 (t, $^3$J = 7.3 Hz, 9H, CH$_3$-TEA) ppm LRMS (ESI−): calcd for C$_{39}$H$_{33}$N$_{10}$O$_7$S$_2^-$ [M − H]$^-$ 817.20 found: 817.13 |

TABLE 3-continued

Examples of fluorogenic azoreductase substrates of the invention

Azoreductase substrates and characterization by $^1$H NMR (300 MHz, DMSO-$d_6$)

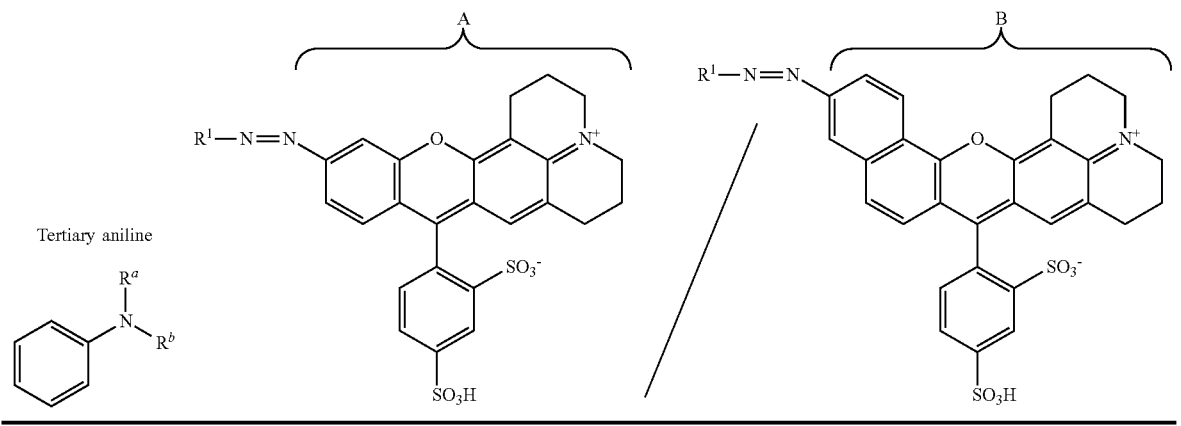

From the previous azo derivatives other fluorogenic azoreductase substrates can be obtained, such as:

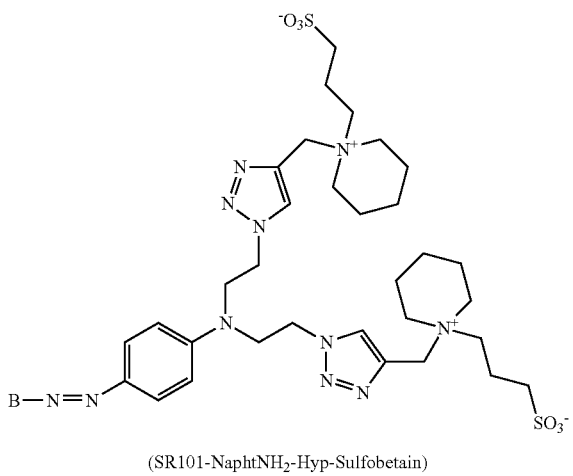

(SR101-NaphtNH$_2$-Hyp-Sulfobetain)

$^1$NMR; δ=8.81 (s, 2H), 8.62 (d, $^3$J=9.0 Hz, 1H), 8.38 (s, 1H), 8.31 (s, 1H), 8.14 (d, $^3$J=9.1 Hz, 1H), 7.85 (m, 2H), 7.75 (m, 2H), 7.32 (d, $^3$J=7.7 Hz, 1H), 7.0.7 (d, $^3$J=7.7 Hz, 1H), 6.90 (m, 3H), 4.65 (bs, 8H), 3.9 (bs, 4H), 3.72 (bs, 2H), 3.63 (bs, 2H), 3.25 (m, 8H), 3.06 (q, $^3$J=7.3 Hz, 6H, CH$_2$-TEA), 2.71 (m, 2H), 2.62 (m, 4H), 2.15 (m, 2H), 1.83 (m, 10H), 1.53 (m, 4H), 1.16 (t, $^3$J=7.3 Hz, 9H, CH$_3$-TEA) ppm. LRMS (ESI−): calcd for $C_{61}H_{71}N_{12}O_{13}S_4^-$ [M−H]$^-$ 1308.42; found, 1308.40
and

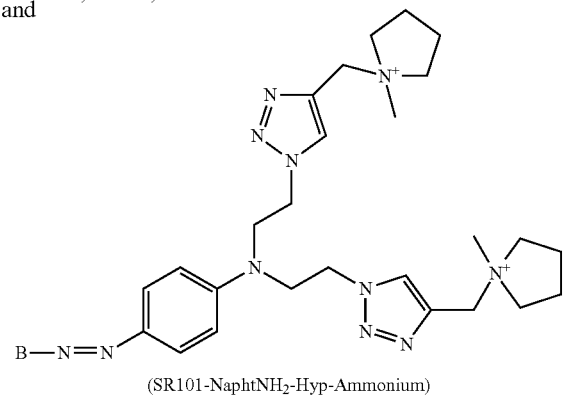

(SR101-NaphtNH$_2$-Hyp-Ammonium)

$^1$H NMR: δ=8.49 (d, $^3$J=9.0 Hz, 1H), 8.44 (s, 2H), 8.33 (s, 1H), 8.29 (bs, 1H), 8.01 (d, $^3$J=9.1 Hz, 1H), 7.89 (m, 2H), 7.75 (m, 2H), 7.68 (m, 2H), 7.35 (d, $^3$J=7.8 Hz, 1H), 7.08 (d, $^3$J=7.8 Hz, 1H), 6.83 (s, 1H), 6.77 (d, 8.1 Hz, 2H), 3.9 (bs, 4H), 4.61 (s, 4H), 3.91 (bs, 4H), 3.72 (bs, 2H), 3.63 (bs, 2H), 3.25 (m, 8H), 2.2-2.0 (m, 8H), ppm. LRMS (ESI+): calcd for $C_{55}H_{61}N_{12}O_7S_2^+$ [M+H]$^+$ 1065.42; found, 1065.73

SR101-NaphtNH$_2$-Hyp-Sulfobetain can be prepared with the following procedure.

SR101-NaphtNH$_2$-(N$_3$)$_2$ (1 equiv.) and 3-(1-(prop-2-yn-1-yl)piperidin-1-ium-1-yl)propane-1-sulfonate (2.1 equiv.) are dissolved in a mixture of dimethylformamide (DMF) and water (1:1, v/v). Aqueous solutions of sodium ascorbate (0.5 equiv.) and CuSO$_4$.5 H$_2$O (0.25 equiv.) are sequentially added and the resulting reaction mixture is stirred at room temperature under an argon atmosphere for 2 h. The reaction is checked for completion by RP-HPLC. After the reaction is completed, the mixture is then diluted with aqueous TEAB (triethylammonium bicarbonate, 50 mM, pH 7.5) buffer and purified by semi-preparative RP-HPLC to give, after lyophilization, a dark blue amorphous powder.

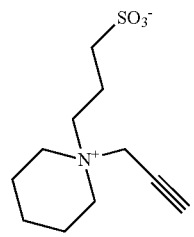

: 3-(1-(prop-2-yn-1-yl)piperidin-1-ium-1-yl)propane-1-sulfonate

Similarly, SR101-NaphtNH$_2$-Hyp-Ammonium is prepared from SR101-NaphtNH$_2$-Hyp-(N$_3$)$_2$ and 1-methyl-1-(prop-2-yn-1-yl)pyrrolidin-1-ium bromide (in replacement of 3-(1-(prop-2-yn-1-yl)piperidin-1-ium-1-yl)propane-1-sulfonate).

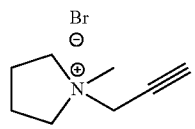

: 1-methyl-1-(prop-2-yn-1-yl)pyrrolidin-1-ium bromide

2. Synthesis of a Fluorogenic Nitroreductase Substrate of the Invention

One strategy for preparing the fluorogenic nitroreductase substrates according to the invention can consist in a nucleophilic aromatic substitution of SR101-Br or SR101-NaphtBr, as generally illustrated by Scheme 9.

Scheme 10: Synthesis of fluorogenic nitroreductase substrates of the invention

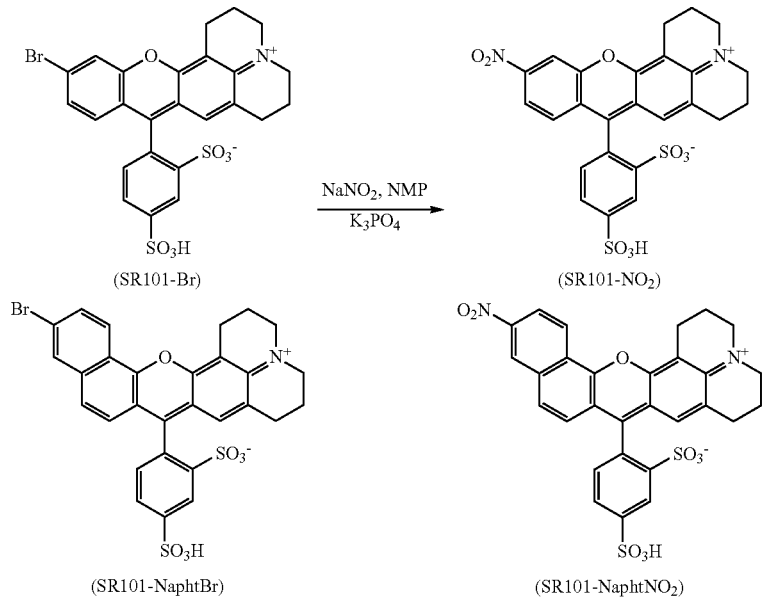

SR101-NO₂ can be prepared using this strategy.

1H). LRMS (ESI−): calcd for $C_{27}H_{22}NO_9S_2^-$ [M−H]⁻ 555.05, found 555.07.

To do this, TFA salt of SR101-Br (1 equiv.), K₃PO₄ (10 equiv.) and NaNO₂ (10 equiv.) are dissolved in NMP (200 μL). The mixture is kept under an argon atmosphere and stirred at room temperature for 12 h. Reaction completion is assessed by RP-HPLC. Thereafter, the crude mixture is diluted with aqueous 0.1% TFA (1.5 mL) and purified by semi preparative RP-HPLC.

SR101-Br was previously prepared using the procedure of previous Scheme 8, achieved with 3-bromophenol as the phenolic partner:

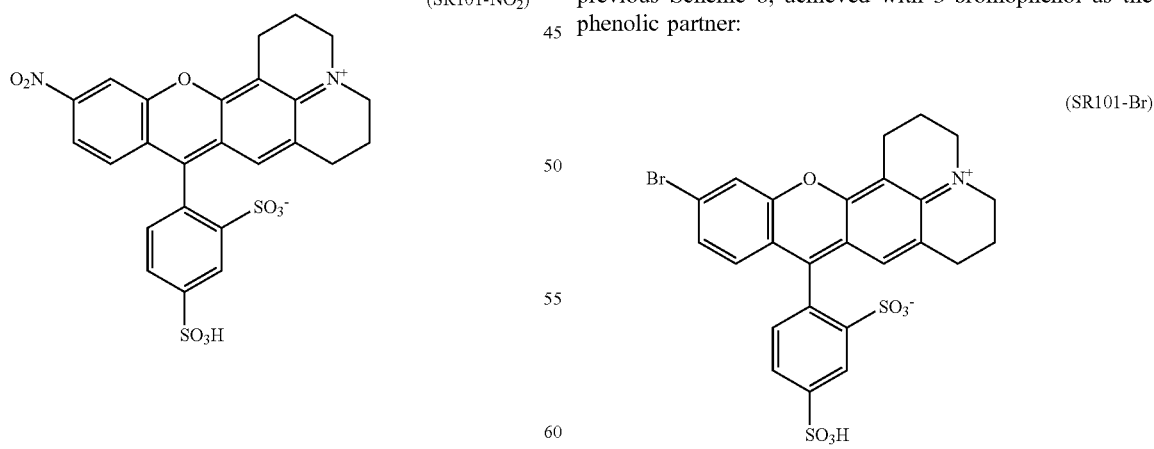

¹H NMR (300 MHz, DMSO-d6): δ=2.02 (bs, 2H), 2.14 (bs, 2H), 2.74 (bs, 2H), 3.09 (bs, 2H), 3.77 (bs, 4H), 6.86 (s, 1H), 7.37 (d, ³J(H—H)=8.7 Hz, 1H), 7.59 (d, ³J(H—H)=7.8 Hz, 1H), 8.12 (dd, ³J(H—H)=8.7 Hz, ⁴J(H—H)=1.5 Hz, 1H), 8.19 (dd, ³J(H—H)=6.9 Hz, ⁴J(H—H)=1.1 Hz, 1H), 8.54 (d, ⁴J(H—H)=1.1 Hz, 1H), 8.59 (d, ⁴J(H—H)=1.5 Hz,

¹H NMR (300 MHz, DMSO-d6): δ=1.90 (bs, 2H), 2.04 (bs, 2H), 2.70 (bs, 2H), 3.0 (bs, 2H), 3.70 (bs, 4H), 6.83 (s, 1H), 7.01 (d, ³J(H—H)=8.6 Hz, 1H), 7.09 (d, ³J(H—H)=7.8 Hz, 1H), 7.56 (dd, ³J(H—H)=8.6 Hz, ⁴J(H—H)=1.8 Hz, 1H) 7.75 (dd, ³J(H—H)=7.8 Hz, ⁴J(H—H)=1.7 Hz, 1H), 8.17 (d, $^4$J(H—H)=1.8 Hz, 1H), 8.25 (d, $^4$J(H—H)=1.7 Hz, 1H) ppm. HRMS (ESI–): calcd for [M–H]$^-$ C$_{25}$H$_{20}$NO$_7$S$_2$$^-$ 587.9792, found 587.9775.

3. Synthesis of Fluorogenic Carboxylesterase Substrates of the Invention a) Preparation of SR101-OAc:

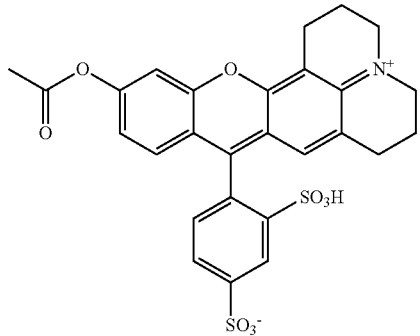

LRMS (ESI–): calcd for C$_{27}$H$_{22}$NO$_9$S$_2$$^-$ [M–H]$^-$ 568.07, found 586.13.

SR101-OH (1 equiv.) is dissolved in acetic anhydride (Ac$_2$O). Dry pyridine (1.2 equiv.) is added dropwise and the resulting reaction mixture is stirred at room temperature for 2 h. The completion of the reaction is checked by RP-HPLC and glacial acetic acid (AcOH) is added to quench the excess of pyridine. Then, the crude mixture is diluted with aqueous 0.1% TFA and directly purified by semi-preparative RP-HPLC.

b) Preparation of SR101-NaphtOAc:

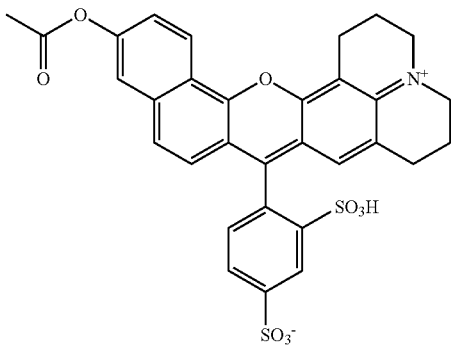

$^1$H NMR (300 MHz, DMSO-d6): δ=8.65 (d, $^3$J=9.1 Hz, 1H), 8.29 (d, $^2$J=1.5 Hz, 1H), 7.82 (d, $^4$J=1.5 Hz, 1H), 7.76 (dd, $^3$J=7.8, $^4$J=1.5 Hz, 1H), 7.65 (m, 2H), 7.18 (d, $^3$J=7.9 Hz, 1H), 7.00 (d, 3J=8.9 Hz, 1H), 6.90 (s, 1H), 3.62-3.71 (m, 4H), 3.2 (bs, 2H), 2.75 (bs, 2H), 2.25 (s, 3H), 2.09 (bs, 2H), 1.92 (bs, 2H) ppm, LRMS (ESI–): calcd for C$_{31}$H$_{24}$NO$_9$S$_2$$^-$ [M–H]$^-$ 618.09, found 618.13

SR101-NaphtOAc is prepared in the same way than SR101-OAc, by replacing SR101-OH by SR101-NaphtOH (1 equiv.) as starting material. Lyophilized, SR101-NaphtOAc appears as a purple amorphous powder.

c) Preparation of SR101-NaphtO-lauric acid:

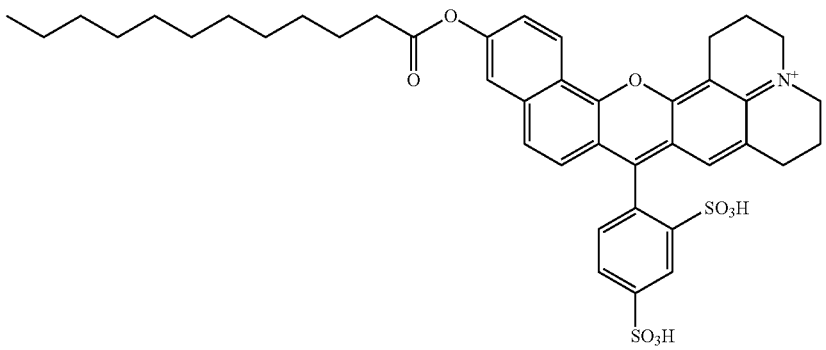 [SMILES: CCCCCCCCCCCC(=O)Oc1ccc2c3c(ccc2c1)C(c1ccc(S(=O)(=O)O)cc1S(=O)(=O)O)=c1cc2c4c(c1O3)CCC[N+]=4CCC2]

$^1$H NMR (300 MHz, CD$_3$OD): δ=8.75 (m, 2H), 8.10 (dd, $^4$J=1.4 Hz, $^3$J=7.9 Hz, 1H), 7.72 (m, 2H), 7.55 (dd, $^4$J=2.2 Hz, $^3$J=6.6 Hz, 1H), 7.40 (d, $^3$J=7.9 Hz, 1H), 7.17 (d, $^3$J=8.9, 1H), 6.99 (s, 1H), 3.70 (m, 4H), 2.80 (m, 2H), 2.16 (m, 2H), 2.01 (m, 2H), 1.76 (m, 2H), 1.29 (m, 20H), 1.17(t, $^3$J=7.0, 3H). LRMS (ESI–): calcd for C$_{41}$H$_{44}$NO$_9$S$_2^-$ 758.24, found 758.23.

SR101-NaphtOH (1 equiv.) is dissolved in dry DMF (500 µL) and TEA (5 equiv.) and lauroyl chloride (5 equiv.) are sequentially added dropwise. The resulting reaction mixture is stirred at 50° C. for 4 h. The completion of the reaction is checked by RP-HPLC and glacial AcOH is added to quench the excess of TEA. The crude mixture is purified by preparative TLC (thick silica layer: 0.25 mm, CH$_2$Cl$_2$/CH$_3$OH (85:15, v/v) as eluent). Finally, the mixture is subjected to an automated flash-purification on a RP-C18 cartridge in order to remove excess of TEA salt. The product-containing fractions are lyophilized to give SR101-NaphtO-lauric acid as a purple solid.

4. Synthesis of Fluorogenic Sulfatase Substrates of the Invention
Preparation of SR101-NaphtO(SO$_3$H)

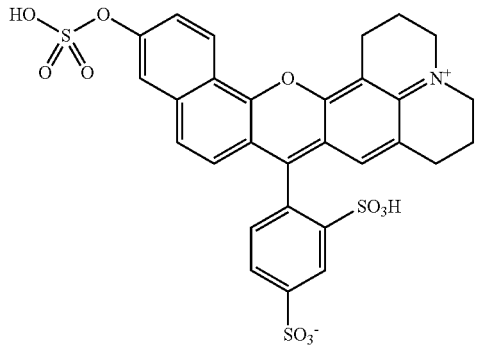

$^1$H (300 MHz, D$_2$O): δ=8.70 (d, $^3$J=9.2 Hz, 1H), 8.29 (d, $^4$J=1.5 Hz, 1H), 7.85 (d, $^4$J=2.2 Hz, 1H), 7.73 (m, 3H), 7.21 (d, $^3$J=7.8 Hz, 1H), 7.01 (d, $^3$J=9.2, 1H), 6.91 (s, 1H), 3.68 (m, 4H), 3.30 (m, 2H, masked by water signal), 3.05 (q, $^3$J=3.0 Hz, 8H, 1.33×N—CH$_2$—CH$_3$, 1.33×TEA), 2.76 (m, 2H), 2.12 (m, 2H), 1.91 (m, 2H), 1.13 (t, $^3$J=3.0 Hz, 12H, 1.33×N—CH$_2$—CH$_3$, 1.33×TEA) ppm. HRMS (ESI+): calcd for [M+H]$^+$ C$_{29}$H$_{24}$NO$_{11}$S$_3^+$ 658.0506, found 658.0520

SR101-NaphtOH (1 equiv.) is dissolved in dry DMF (300 µL) and SO$_3$.Me$_3$N complex (30 equiv.) is added. The resulting reaction mixture is stirred at room temperature overnight. Thereafter, diethyl ether (Et$_2$O) is added and the newly formed precipitate is recovered by centrifugation and subsequently purified by semi-preparative RP-HPLC to give the TEA salt of SR101-NaphtO(SO$_3$H) as a purple solid.

5. Synthesis of Fluorogenic Phosphatase Substrates of the Invention
a) Preparation of SR101-NaphtO(PO(OBn)$_2$)

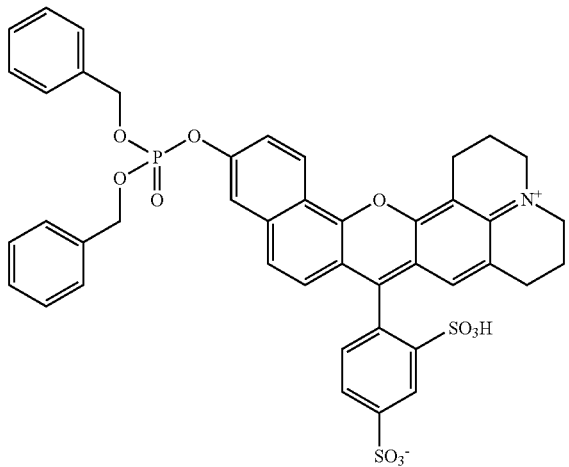

$^1$H NMR (300 MHz, DMSO-d$_6$): δ=8.76 (d, $^3$J=9.2 Hz, 1H), 8.30 (d, $^3$J=1.2 Hz, 1H), 7.75 (m, 4H), 7.36 (m, 10H), 7.22 (d, $^3$J=7.8 Hz, 1H), 7.09 (d, $^3$J=8.9 Hz, 1H), 6.93 (s, 1H), 5.24 (d, $^3$J=8.7 Hz, 4H), 3.7 (m, 4H), 3.22 (m, 2H, masked by DMSO signal), 2.75 (m, 2H), 2.10 (m, 2H), 1.92 (m, 2H) ppm.

SR101-NaptOH (1 equiv.) is dissolved in dry CH$_3$CN. DMAP (4-N,N-dimethylaminopyridine; 0.3 equiv.), CCl$_4$ (tetrachloromethane; 5 equiv.) and DIEA (N,N-diisopropylethylamine: 2.1 equiv.) are sequentially added and the resulting mixture is stirred at 0° C. Then, dibenzylphosphite (1.45 equiv.) is added and the resulting reaction mixture is kept under stirring at 0° C. for 30 min, then at room temperature for 2 h.

Thereafter, the mixture is concentrated under reduced pressure and Et$_2$O is added. The newly formed precipitate is recovered by centrifugation and purified by semi-preparative RP-HPLC, to give the TFA salt of SR101-NaphtO(PO(OBn)$_2$) as a purple solid.

b) Preparation of SR101-NaphtO(PO$_3$H$_2$)

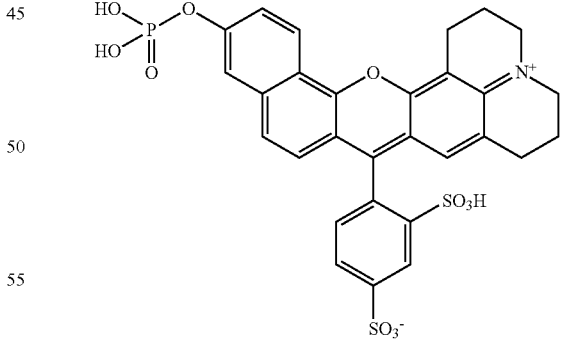

$^1$H NMR (300 MHz, DMSO-d$_6$): δ=8.64 (d, $^3$J=9.1 Hz, 1H), 8.29 (d, $^2$J=1.6 Hz, 1H), 7.83 (d, $^4$J=1.6 Hz, 1H), 7.76 (dd, $^3$J=7.8, $^4$J=1.6 Hz, 1H), 7.67 (m, 2H), 7.19 (d, $^3$J=7.9 Hz, 1H), 6.99 (d, $^3$J=8.9 Hz, 1H), 6.90 (s, 1H), 3.67 (m, 4H), 3.2 (m, 2H), 3.05 (q, $^4$J=3.0 Hz, 10H, 1.66×N—CH$_2$—CH$_3$, 1.66×TEA), 2.74 (m, 2H), 2.10 (m, 2H), 1.92 (m, 2H), 1.15 (t, $^3$J=3.0 Hz, 15H, 1×N—CH$_2$—CH$_3$, 1.66×TEA) ppm. LRMS (ESI–): calcd for C$_{29}$H$_{23}$NO$_{11}$PS$_2^-$ [M–H]$^-$ 656.06, found 656.20.

SR101-NaphtO(PO(OBn)₂) (1 equiv) is dissolved in a mixture of trifluoroacetic acid (TFA) and water (10:1, v/v), and the resulting solution is stirred at room temperature for 2 h. Thereafter, the crude is concentrated under reduced pressure and directly purified by semi-preparative RP-HPLC, to give after lyophilization the TEA salt of the targeted fluorogenic substrate, as a purple solid.

6. Synthesis of Fluorogenic Peptidase Substrates of the Invention a) Preparation of SR101-NHAc

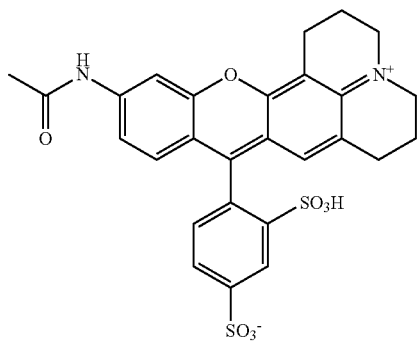

LRMS (ESI−): calcd for $C_{27}H_{23}N_2O_8S_2$ [M−H]⁻ 567.08, found 567.12.

SR101-NH₂ (1 equiv.) is dissolved in Ac₂O (concentration: 0.1 M) and dry pyridine (4 equiv.) is added. The resulting reaction mixture is stirred at 80° C. for 3 h. Thereafter, the mixture is poured into diethyl ether and the resulting precipitate is collected by filtration and subsequently purified by semi-preparative RP-HPLC to give after lyophilization the targeted fluorogenic substrate, as a red solid.

b) Preparation of Gly-SR101-110, β-Ala-SR101-110 and L-Pro-SR101-110

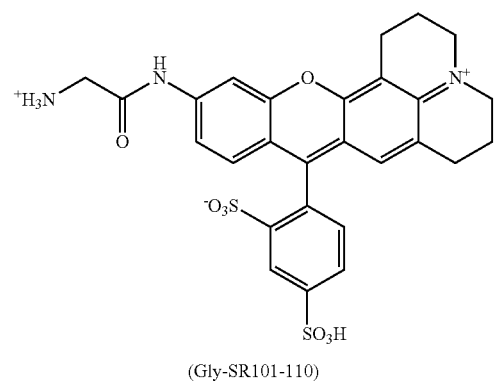

(Gly-SR101-110)

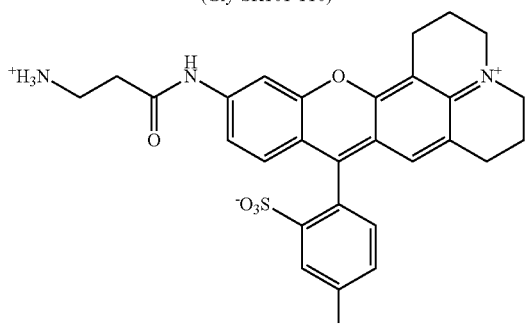

(β-Ala-SR101-110)

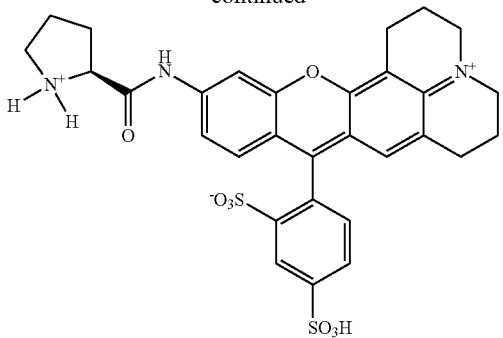

L-Pro-SR101-110

These fluorogenic peptidase substrates can be prepared according to the strategy summarized in Scheme 11 (see below), in combination with the synthetic details summarized in Table 4 (see below).

Scheme 11: Synthesis of fluorogenic Pept.-SR101-110

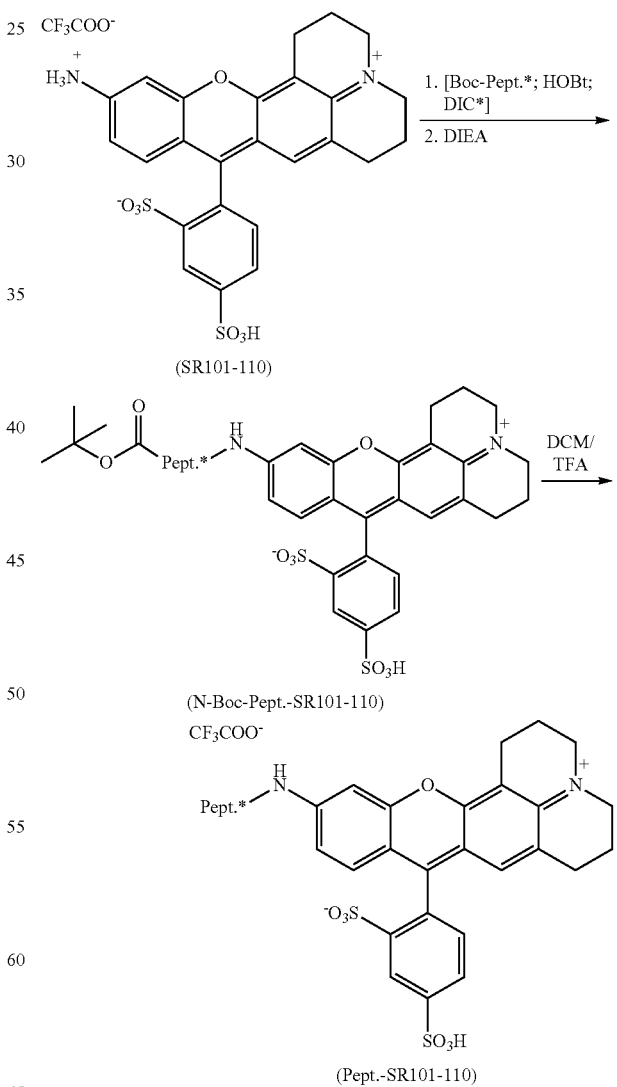

*DIC: Diisopropylcarbodiimide
*Pept.: peptide or amino acide residue

The peptidase-sensitive fluorogenic substrates, as well as their reaction intermediates, were analyzed by RP-HPLC. The obtained results, as well as the used materials and conditions, are summarized in below Table 4.

TABLE 4

| | | |
|---|---|---|
| Gly-SR101-110: | 12.4 min | |
| N-Boc-Gly-SR101-110: | 18.0 min | |
| β-Ala-SR101-110: | 13.9 min | |
| N-Boc-β-Ala-SR101-110: | 20.6 min | |
| Syncronis ™ HPLC column 150 mm × 4.6 mm, | 5 µm | |
| Debit: | 1 mL/min | |

| Eluant gradient: | | |
|---|---|---|
| t (min) | % CH$_3$CN | % H$_2$O 0.1% TFA |
| 0 | 5 | 95 |
| 5 | 5 | 95 |
| 40 | 100 | 0 |
| 42 | 100 | 0 |
| 45 | 5 | 95 |
| 62 | 5 | 95 |

| | | |
|---|---|---|
| L-Pro-SR101-110 (2 atropoisomers): | 13.1 and 13.9 min | |
| N-Boc-L-Pro-SR101-110: (2 atropoisomers) | 18.6 and 18.7 min | |
| Hypersil GOLD HPLC column 150 mm × 4.6 mm, | 5 µm | |
| Debit: | 1 mL/min | |

| Eluant gradient: | | |
|---|---|---|
| t (min) | % CH$_3$CN | % H$_2$O 0.1% TFA |
| 0 | 5 | 95 |
| 5 | 5 | 95 |
| 40 | 100 | 0 |
| 42 | 100 | 0 |
| 45 | 5 | 95 |
| 62 | 5 | 95 | c) Preparation of L-Pyr-SR101-110

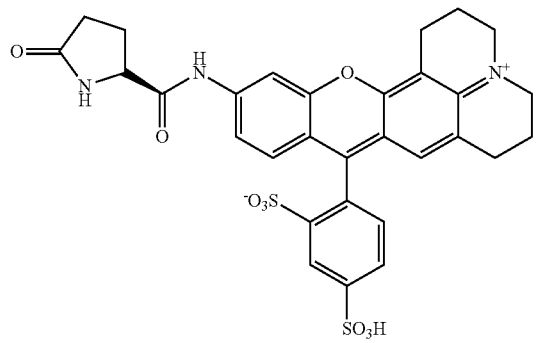

(L-Pyr-SR101-110)

L-Pyr-SR101-110 was obtained by a direct coupling reaction between L-pyroglutamate and SR101-110, carried out with conditions extrapolated from the method for preparing peptidase substrates as previously disclosed.

L-Pyr-SR101-110 so prepared was analyzed by RP-HPLC, under the same conditions as for Gly-SR101-110 and β-Ala-SR101-110. Two atropoisomers were obtained, with as retention times: 15.4 min and 15.9 min.

7. Synthesis of Fluorogenic Myeloperoxidase Substrates of the Invention

Preparation of SR101-NaphtO(para-aminophenyl)

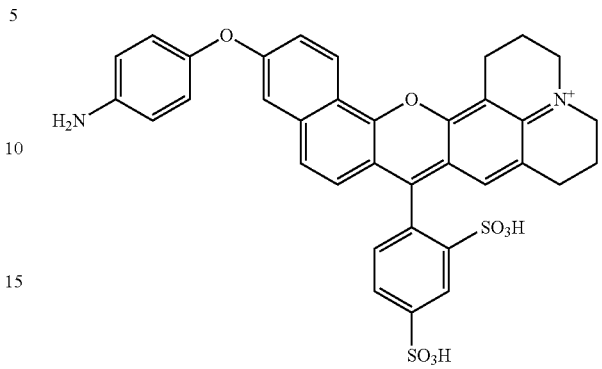

$^1$H NMR (600 MHz, DMSO-d$_6$): δ=8.74 (d, $^3$J=9.2 Hz, 1H), 8.28 (d, $^4$J=1.7 Hz, 1H), 7.77 (dd, $^3$J=7.8 Hz, $^4$J=1.7 Hz, 1H), 7.65 (s, $^3$J=8.9 Hz, 1H), 7.54 (dd, $^3$J=9.1 Hz, $^4$J=2.5 Hz, 1H), 7.28 (d, $^4$J=2.5 Hz, 1H), 7.20 (d, $^3$J=7.8 Hz, 1 H), 6.96 (d, $^3$J=9.0 Hz, 1 H), 6.90 (m, 2H), 6.66 (d, $^3$J=6.7 Hz, 1H), 5.1 (s, 1H), 3.68 (m, 4H), 3.40 (m, 2H, masked by DMSO signal), 2.75 (m, 2H), 2.10 (m, 2H), 1.90 (m, 2H). LRMS (ESI−): calcd for C$_{35}$H$_{27}$N$_2$O$_8$S$_2^-$ [M−H]$^-$ 667.12, found 667.15.

SR101-NaphtO(para-nitrophenyl) (1 equiv.) is dissolved in a mixture H$_2$O/CH$_3$OH (1:1, v/v, 5.0 mL) and Pd/C (10 wt. % loading, 30 mg) is added and the resulting mixture is kept under an argon atmosphere. Then, H$_2$ atmosphere is established and the reaction mixture is stirred at room temperature for 4 h. The completion of the reaction is checked by RP-HPLC. Thereafter, the solution is filtered through a pad of Celite 545, washed with CH$_3$OH (50 mL) and concentrated under reduced pressure. The crude mixture is purified by semi-preparative RP-HPLC to give the TFA salt of SR101-NaphtO(para-aminophenyl) as a purple solid.

Preparation of SR101-NaphtO(para-nitrophenyl)

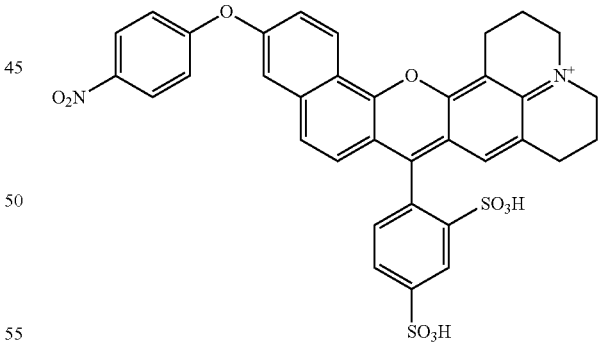

$^1$H NMR (300 MHz, CD$_3$OD): δ=8.85 (d, $^3$J=9.1 Hz, 1H), 8.30 (m, 3H), 7.85 (d, $^4$J=2.4 Hz, 1H), 7.79 (m, 2H), 7.72 (dd, $^3$J=9.1 Hz, $^4$J=2.4 Hz, 1H), 7.36 (m, 2H), 7.22 (d, $^3$J=7.8 Hz, 1 H), 7.22 (d, $^3$J=8.9 Hz, 1 H), 6.93 (s, 1H), 3.70 (m, 4H), 3.21 (m, 2H), 2.80 (m, 2H), 2.10 (m, 2H), 1.92 (m, 2H). LRMS (ESI−): calcd for C$_{35}$H$_{25}$N$_2$O$_{10}$S$_2^-$ [M−H]$^-$ 697.09, found 697.47.

SR101-NaphtOH (1 equiv.) is dissolved in dry DMF (1 mL), and K$_2$CO$_3$ (5 equiv.) and 1-fluoro-4-nitrobenzene (3 equiv.) are sequentially added. The resulting reaction mixture is stirred overnight at 50° C. The completion of the reaction is checked by RP-HPLC. Thereafter, diethyl ether is added and the newly formed precipitate is recovered by centrifugation and subsequently purified by semi-preparative RP-HPLC to give the TFA salt of SR101-NaphtO(para-nitrophenyl) as a purple solid.

Example 2

Use of the Fluorogenic Substrates of Formula I According to the Invention to Detect a Targeted Enzyme Activity A) Use of SR101-$NO_2$ for Detecting a Nitroreductase Activity 1. Use of SR101-$NO_2$ with a Purified Nitroreductase A kinetic study was carried out by incubating the substrate SR101-$NO_2$ in PBS at 37.5° C., at a concentration of about 5 μM.

Successive additions of NADH and nitroreductase from *Escherichia coli* (NfsA=4×2.5 μg) were performed and the fluorescence at 575 nm (emission maximum of SR101-110) was measured, under an excitation wavelength of 500 nm. The obtained results (FIG. 1a) shows the evolution of the intensity of fluorescence obtained during this study.

The addition of NADH (0.5 mM) did not influence the evolution of the fluorescence that appears only after the first addition of 2.5 μg of nitroreductase. A first level was reached, and 3 further additions of enzyme, to a total amount of 10 μg, were necessary for a complete reduction of the 5 μM of SR101-$NO_2$, after an hour of incubation at 37.5° C.

Figure 1B:
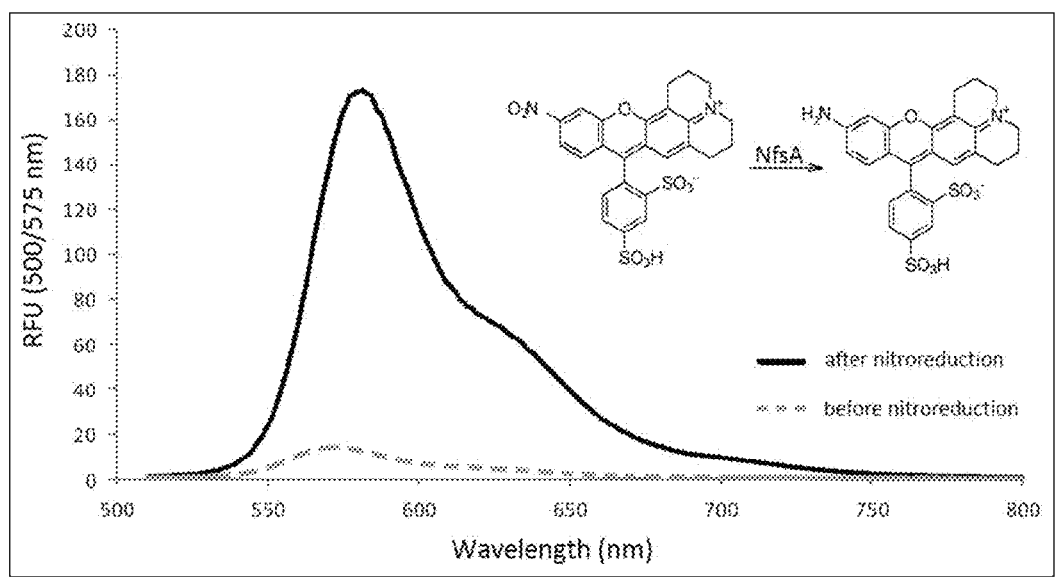
FIG. 1b is a graphic showing two red fluorescence emission spectra, related to two states of a reaction medium comprising a particular fluorogenic substrate of the invention (SR101-NO$_2$)

The emitted fluorescence was recorded before and after the reduction of SR101-$NO_2$, showing a quenching efficiency of 92% with a fluorescence enhancement of a factor of 15 (see FIG. 1b).

2. Use of SR101-$NO_2$ for Detecting a Nitroreductase Activity in Microorganisms The reduction of SR101-$NO_2$ by an *E. coli* strain (ATCC 25922), known for its nitroreduction ability, was analyzed in fluorescence.

This kinetic study was carried out with an initial concentration of cells around $10^6$ cfu/ml, growing in Trypcase Soya Broth at 37° C., in presence of different concentrations of fluorogenic substrate (from 0 μM to 100 μM). For this study, said fluorogenic substrate is used in the form of a SR101-110/SR101-$NO_2$ (with a ratio of about 10/90).

Figure 1C:
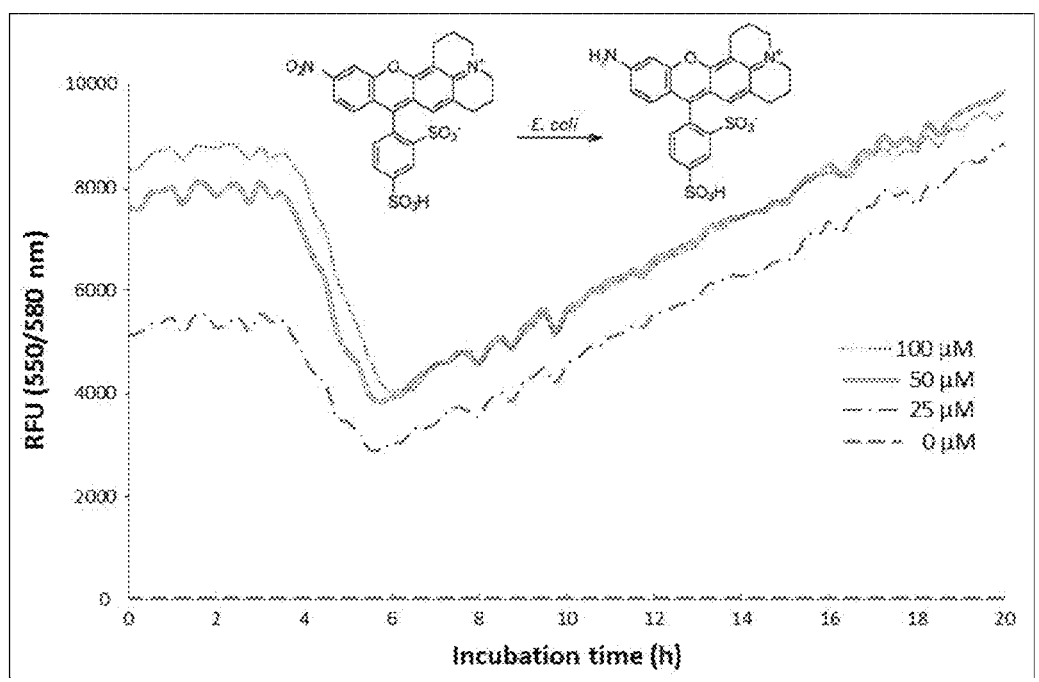
FIG. 1c is a graphic showing the kinetic reduction of a SR101-110/SR101-NO$_2$ mixture, by an *Escherichia coli* strain.

The fluorescence at 580 nm was measured, under an excitation wavelength of 550 nm. The evolution of this intensity of fluorescence is presented in FIG. 1c.

At the beginning of the assay, a relatively high fluorescence is detected. It is caused by the presence of SR101-110 initially present in the medium. This fluorescence rapidly decreases with the growth of the cells. Then, it progressively increases revealing the progressive nitroreduction of SR101-$NO_2$.

B) Use of SR101-Q-$CO_2$H for Detecting an Azoreductase Activity

1. Use of SR101-Q-$CO_2$H with a Purified Azoreductase

A kinetic study was carried out by incubating the substrate SR101-Q-$CO_2$H in phosphate buffer at 37° C., at a concentration of about 100 μM in presence of NADPH (500 or 1000 μM), FMN (5 μM) and 10 mg/L of azoreductase (AzoR) from *E. coli* (Mercier C. et al., J. Appl. Microb., 2013, 15: 1012-1022). The fluorescence emission at 580 nm was measured, upon excitation at 550 nm.

Figure 2:
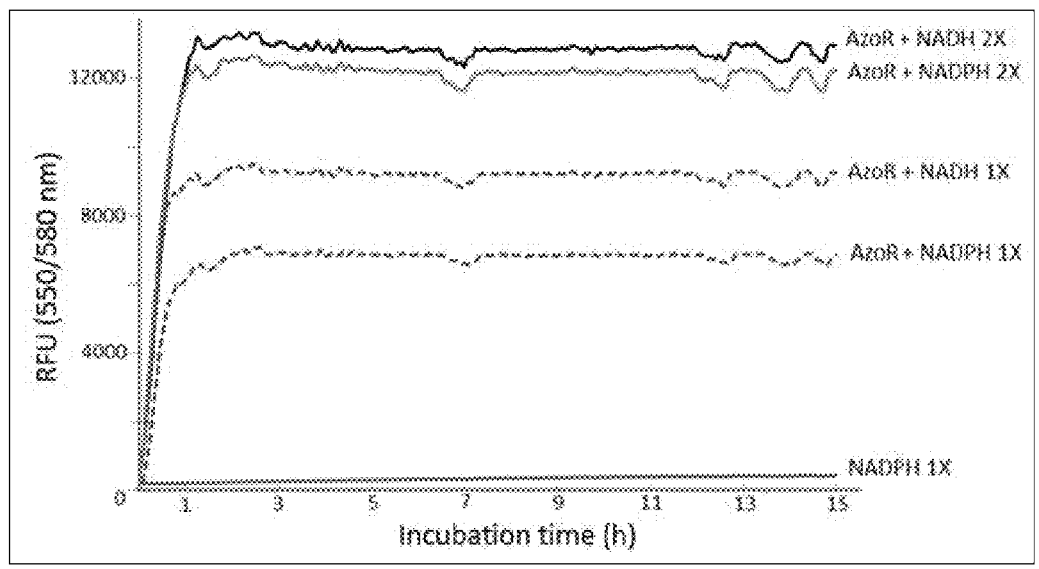
FIG. 2 is a graphic showing the appearance of a fluorescence and the enhancement of its intensity indicating the azoreduction of SR101-Q-CO$_2$H.

In presence of the azoreductase, AzoR, and various concentrations of NADH or NADPH (1×=500 μM, 2×=1000 μM), the obtained results (FIG. 2) shows the evolution of the intensity of fluorescence obtained. The reduction of SR101-Q-$CO_2$H is quite instantaneous and is limited by the amount of NADH or NADPH available. In absence of AzoR, there is quite no reduction by NADH (not shown) or NADPH even after 15 hours of incubation.

2. Use of SR101-Q-$CO_2$H for Detecting an Azoreductase Activity in Microorganisms a) The bacterial reduction of SR101-Q-$CO_2$H was compared to the one of Methyl Red, an azo dye. Each molecule at 100 μM in Trypcase Soya Broth in presence 7.5*$10^7$ colonies forming unit (cfu) of *E. coli* K12 was incubated overnight at 37° C. The fluorescence produced by the azoreduction of Methyl Red was measured at 395 nm under an excitation wavelength of 250 nm. The fluorescence produced by the azoreduction of SR101-Q-$CO_2$H was measured at 580 nm under an excitation wavelength of 550 nm. For Methyl Red the ratio between medium with and without bacteria was 469/184 (×2.5). For SR101-Q-$CO_2$H, it was 19 times upper: 17269/363 (×48).

b) The capacity of strains belonging to different species of microorganisms to reduce SR101-Q-$CO_2$H in Trypcase Soya Broth was followed for 24 hours at 37° C. Various concentrations of SR101-Q-$CO_2$H (5; 10; 20; 50; 100 μM) were tested. The selection of strains covers pathogenic or frequently encountered species: 1 yeast strain (*Candida albicans*), 3 gram negative bacteria (*E. coli, Pseudomonas aeruginosa* and *Salmonella typhimurium*) and 3 gram positive bacteria (*Enterococcus faecalis, Listeria monocytogenes, Staphylococcus epidermidis*). The initial concentration of cells was around $10^5$ cfu for bacteria and $10^4$ for the yeast. The fluorescence at 580 nm was measured, under an excitation wavelength of 550 nm.

Figure 3:
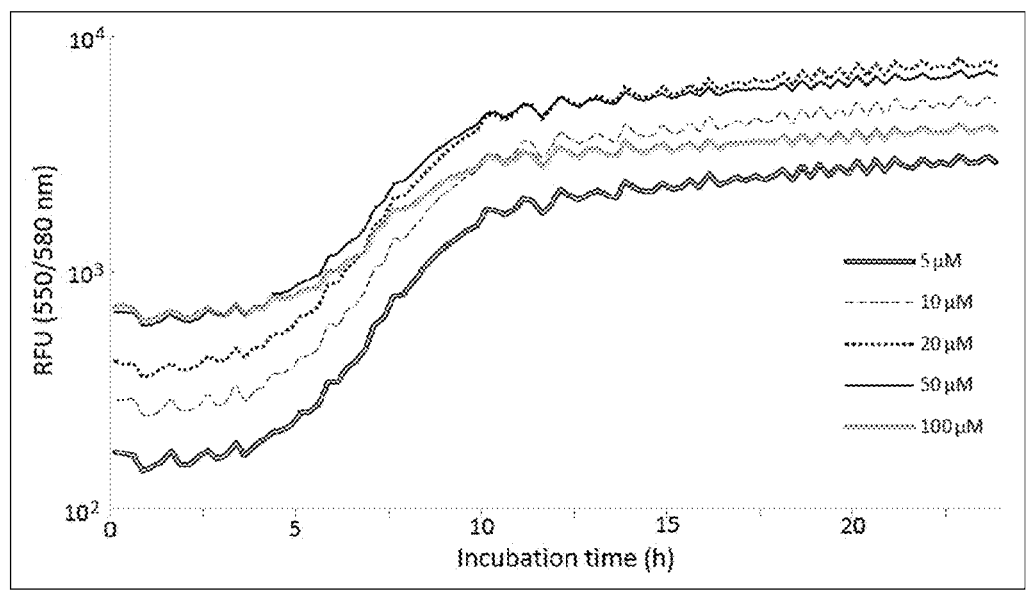
FIG. 3 is a graphic showing the appearance of a fluorescence and the enhancement of its intensity indicating the azoreduction of SR101-Q-CO$_2$H, at different concentrations, by *Candida albicans*.

For *C. albicans*, the optimal concentration of SR101-Q-$CO_2$H was 20 μM, as the final level of fluorescence was as high as at 50 μM but with a lower level of initial fluorescence (FIG. 3).

Figure 4A:
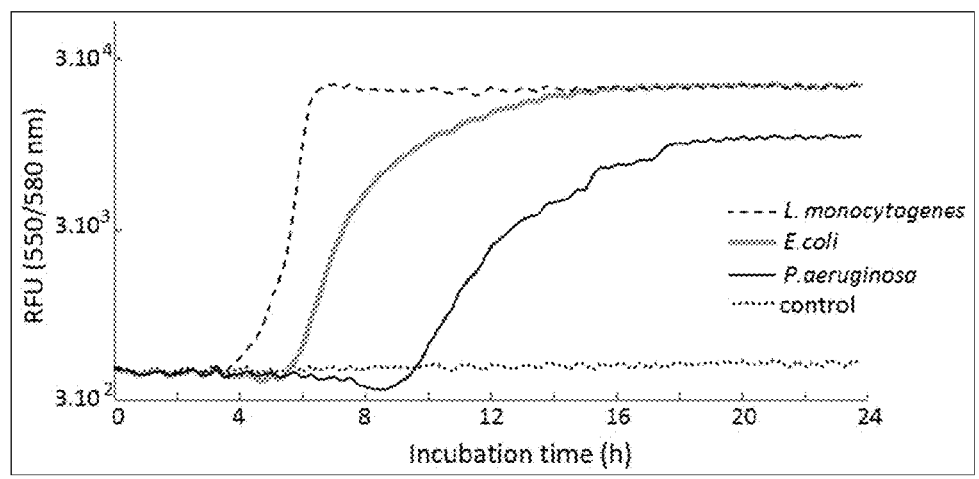
FIG. 4a and FIG. 4b are graphics showing the appearance of a fluorescence and the enhancement of its intensity indicating the azoreduction of SR101-Q-CO$_2$H, performed by different microorganisms.
Figure 4B:
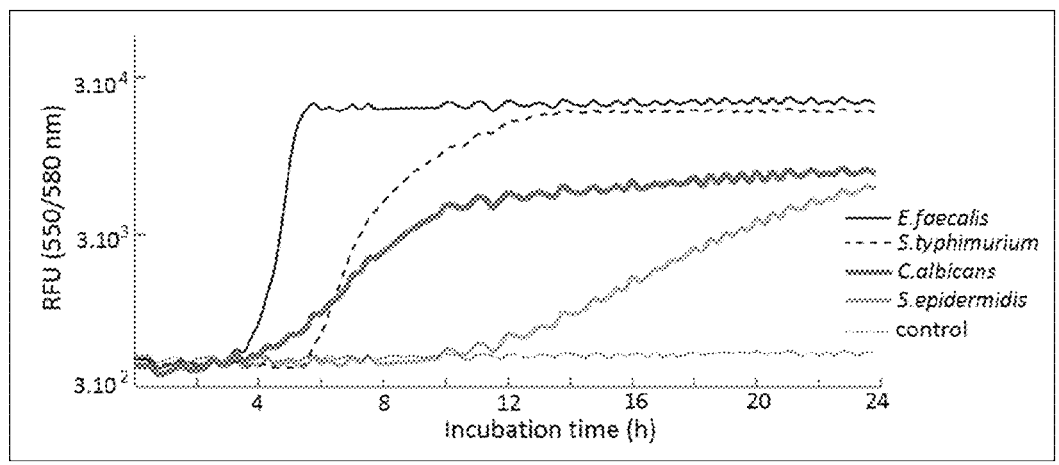

All of the tested organisms reduced SR101-Q-$CO_2$H, generating a high level of fluorescence even at a low concentration of the fluorogenic substrate (FIG. 4a and FIG. 4b).

C) Use of SR101-NaphtOAc or SR101-NaphtO-lauric Acid for Detecting a Carboxylesterase Activity 1. A kinetic study of SR101-NaphtOAc was carried out by incubating this fluorogenic substrate, previously solubilized in phosphate buffered saline (pH 7.4) at a concentration of about 5 μM, with 10 units of pig liver esterase (PLE), at 37° C.

Figure 5A:
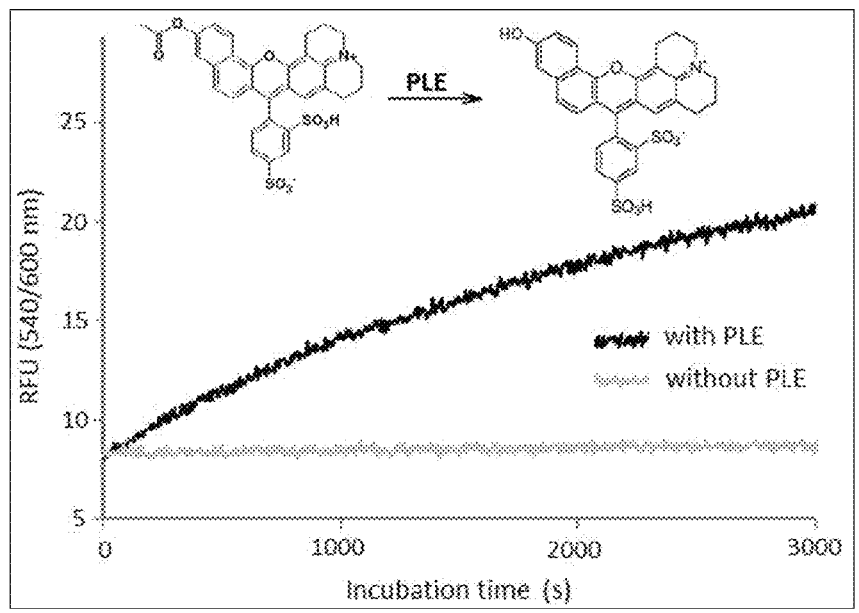

The evolution of the intensity of fluorescence at 600 nm, emitted under an excitation wavelength of 540 nm, was recorded and is presented in FIG. 5a.

As shown, a remarkable fluorescence enhancement is observed after the adjunction of the carboxyl esterase.

2. A kinetic study of SR101-NaphtO-lauric acid was carried out by incubating this fluorogenic substrate, previously solubilized in phosphate buffered saline (pH 7.4) at a concentration of about 5 μM, with 10 units of pig liver esterase (PLE), at 37° C.

Figure 5B:
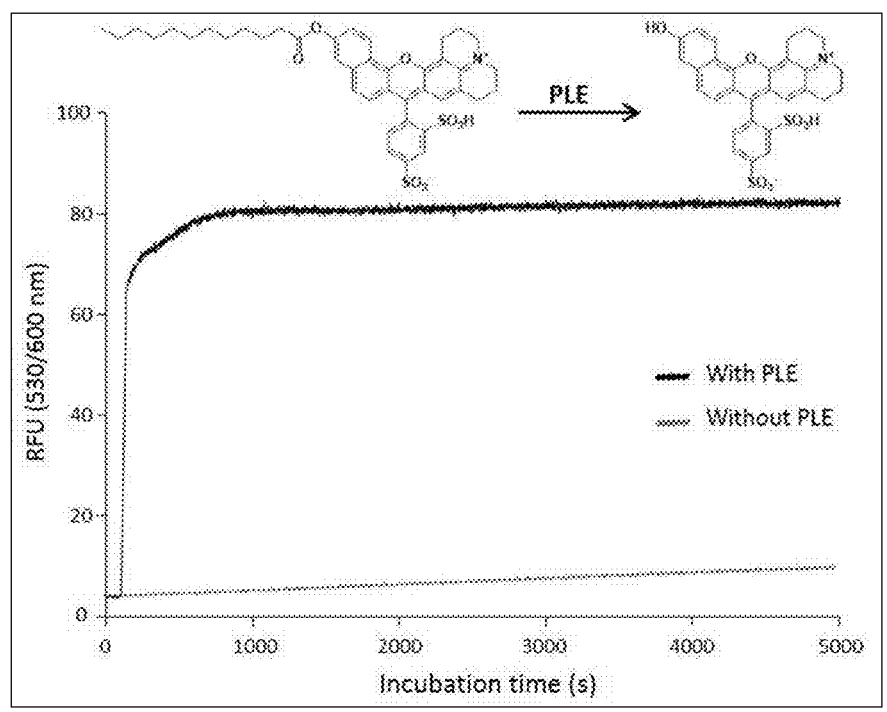

The evolution of the intensity of fluorescence at 600 nm, emitted under an excitation wavelength of 530 nm, was recorded and is presented in FIG. 5b.

As shown, a remarkable fluorescence enhancement is observed after the addition of the enzyme.

D) Use of SR101-NaphtO($SO_3$H) for Detecting a Sulfatase Activity

A kinetic study of SR101-NaphtO($SO_3$H) was carried out by incubating this fluorogenic substrate, previously solubilized in phosphate buffered saline (pH 7.4) at a concentration of about 10 μM, with 7.8 units of a sulfatase from *Helix pomatia*, at 37° C.

Figure 6:
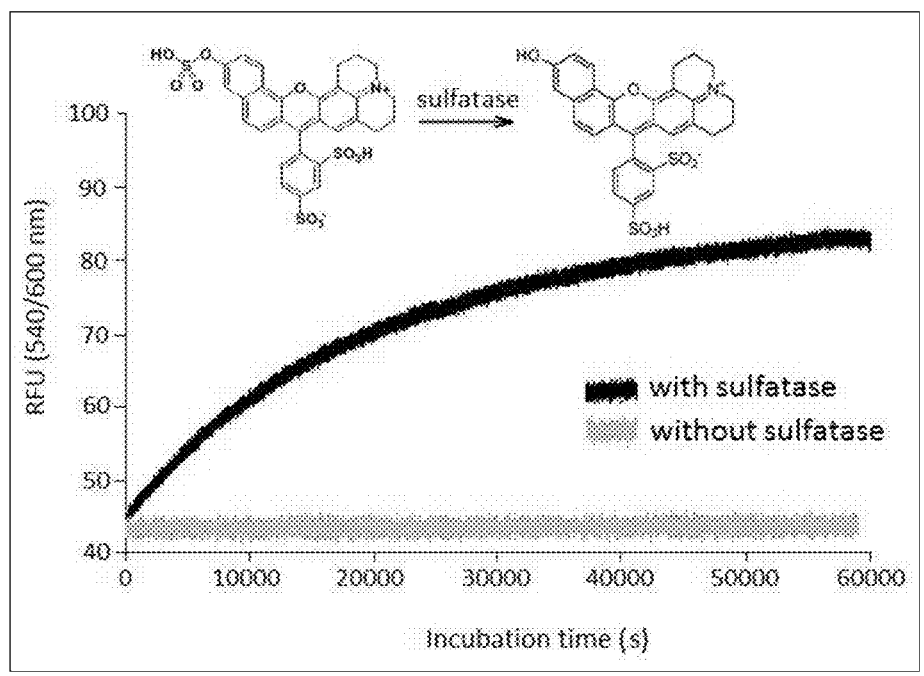

The evolution of the intensity of fluorescence at 600 nm, emitted under an excitation wavelength of 540 nm, was recorded and is presented in FIG. 6.

As shown, a remarkable fluorescence enhancement is observed after the addition of the enzyme.

E) Use of SR101-NaphtO(para-aminophenyl) for Detecting a Myeloperoxidase Activity A kinetic study of SR101-NaphtO(para-aminophenyl) acid was carried out by incubating this fluorogenic substrate, previously solubilized in phosphate buffered saline (pH 7.4) at a concentration of about 10 μM, with 150 equivalents of sodium hypochlorite, at 25° C.

This chemical procedure using sodium hypochlorite is routinely used to simulate a myeloperoxidase activity (Shepherd et al., Chemistry and Biology, 2007, 14: 1221-1231).

Figure 7:
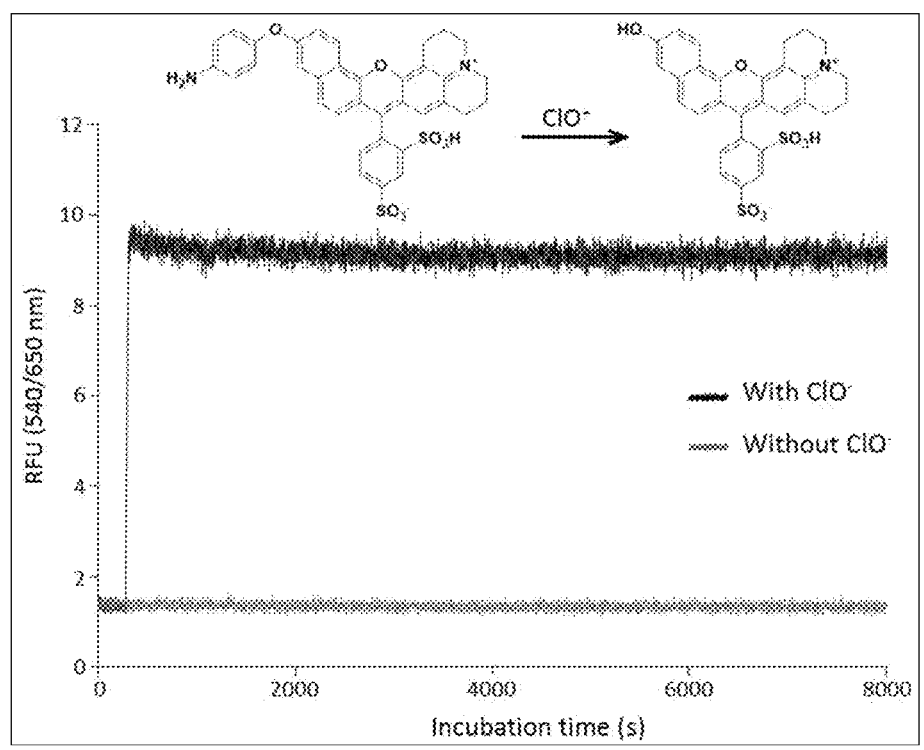

The evolution of the intensity of fluorescence at 650 nm, emitted under an excitation wavelength of 540 nm, was recorded and is presented in FIG. 7.

As shown, a remarkable fluorescence enhancement is observed after the addition of sodium hypochlorite (ClO⁻).

The invention claimed is:

1. A fluorogenic substrate of formula I or II:

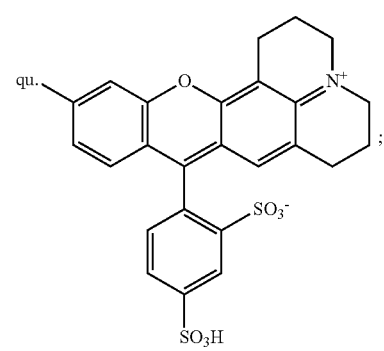
(I)

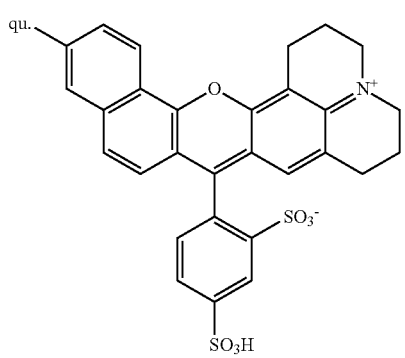
(II)

wherein qu. is a fluorescence quencher group selected from the group consisting of:

—$NO_2$;

—N=N—$R^1$; $R^1$ being any organic group that does not obscure the corresponding azo bond;

—NHCO-Pept.; Pept. being a peptide residue or any organic group that does not obscure the corresponding amide bond;

—O-Glyc.; Glyc. being an oligoglycoside residue that does not obscure the corresponding glycosidic bond;

—O—C(O)—$R^2$; —O—P(O)($OR^2$)($OR^{2\prime}$) and —O—S($O)_2$—$R^2$; $R^2$ and $R^{2\prime}$ being independently a hydrogen atom or any organic group that does not obscure the corresponding ester bond; and

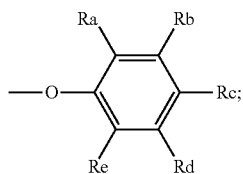

$R_a$, $R_b$, $R_c$, $R_d$ and $R_e$ being independently a hydrogen atom or any organic group that does not obscure the corresponding arylether bond.

2. The fluorogenic substrate of claim 1, wherein qu. is —$NO_2$.

3. The fluorogenic substrate of claim 1, wherein qu. is —N=N—$R^1$.

4. The fluorogenic substrate of claim 1, wherein qu. is —O—C(O)—$R^2$; —O—P(O)($OR^2$)($OR^{2\prime}$) or —O—S($O)_2$—$R^2$.

5. The fluorogenic substrate of claim 1, wherein qu. is

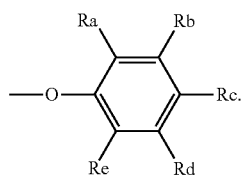

6. A method for detecting an enzyme activity of a microorganisms selected from the group consisting of nitroreductase, azoreductase, peptidase, glycosidase, esterase and myeloperoxidase activities, comprising the following steps:

a) providing a reaction medium comprising at least one fluorogenic substrate of formula (I) or (II):

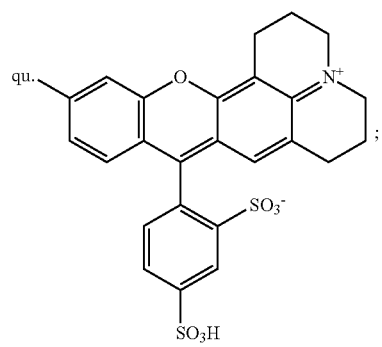
(I)

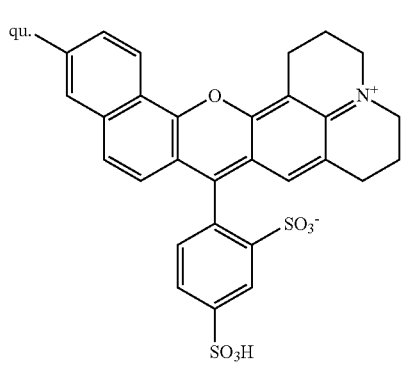
(II)

wherein qu. is a fluorescence quencher group selected from the group consisting of:
—NO₂;
—N=N—R¹; R¹ being any organic group that does not obscure the corresponding azo bond;
—NHCO-Pept.; Pept. being a peptide residue or any organic group that does not obscure the corresponding amide bond;
—O-Glyc.; Glyc. being an oligoglycoside residue that does not obscure the corresponding glycosidic bond;
—O—C(O)—R²; —O—P(O)(OR²)(OR²') and —O—S(O)₂—R²; R² and R²' being independently a hydrogen atom or any organic group that does not obscure the corresponding ester bond; and

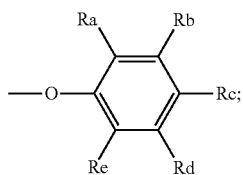

$R_a$, $R_b$, $R_c$, $R_d$ and $R_e$ being independently a hydrogen atom or any organic group that does not obscure the corresponding arylether bond;
in accordance with the enzyme activity to detect,
b) inoculating the reaction medium with a biological sample to be tested,
c) incubating inoculated medium, and
d) detecting whether there is an appearance or increase of an orange, far-red or near infra-red fluorescence.

7. A reaction medium for the detection and/or identification of microorganisms, comprising at least one fluorogenic substrate of claim 1.

8. A fluorescent compound of formula (I″) or (II″):

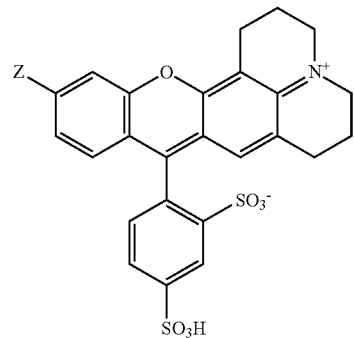

(I″)

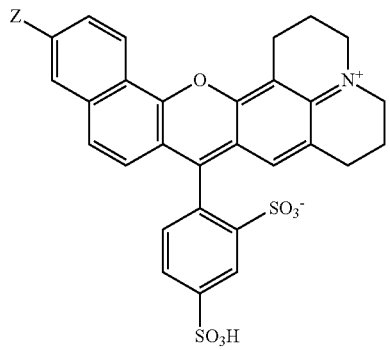

(II″)

wherein Z is —NH₂ or —OH.

9. The fluorescent compound of claim 8, selected from the group consisting of:

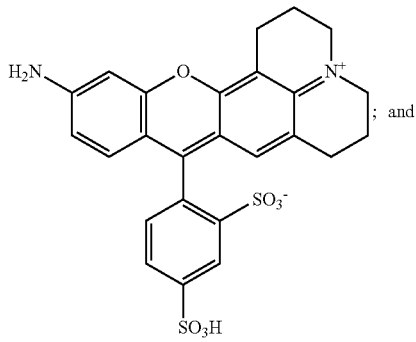

; and

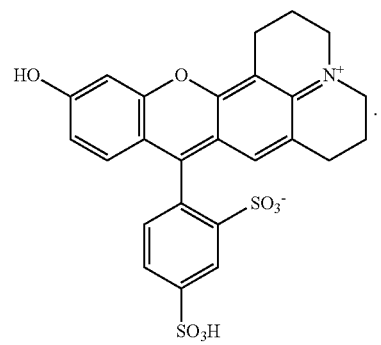

10. The fluorescent compound of claim 8, selected from the group consisting of:

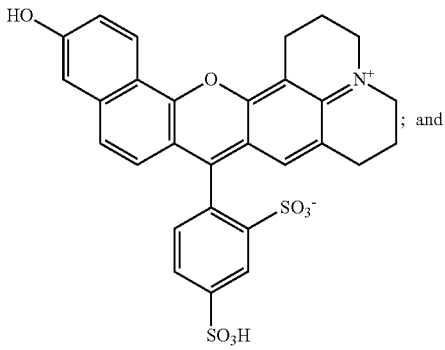

; and

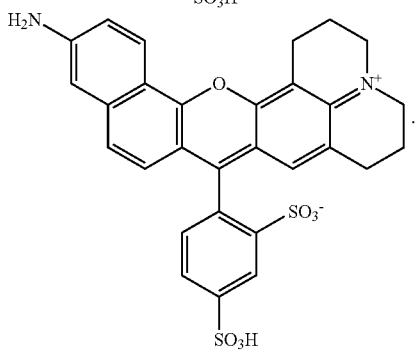

11. The fluorogenic substrate of claim 1, wherein qu. is —N═N—R with R being selected from the group consisting of:

4-(N-butanoate, N-methyl)anilinyl;
4-(N-azidoethyl, N-methyl)anilinyl;
4-amino(N-methyl, N-ethylaniline)phenyl;
4-(N-3-maleimidylpropyl,N-methyl)anilinyl;
4-(N-3-aminopropyl,N-methyl)anilinyl;
4-(N,N-dimethyl)anilinyl;
4-(N,N-di-3-azidoethyl)anilinyl;
1,1'-((1,1'-((phenylazanediyl)bis(ethane-2,1-diyl))bis(1H-1,2,3-triazole-4,1-diyl))bis(methylene))bis(1-methylpyrrolidin-1-ium); and
3,3'-(1,1'-((1,1'-((phenylazanediyl)bis(ethane-2,1-diyl))bis(1H-1,2,3-triazole-4,1-diyl))bis(methylene))bis(piperidine-1-ium-1,1-diyl))bis(propane-1-sulfonate).

12. The fluorogenic substrate of claim 1, selected from the group consisting of:

SR101-NO₂

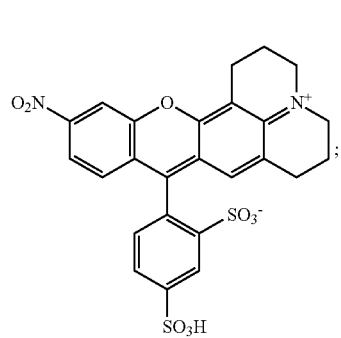

SR101-Q-CO₂H

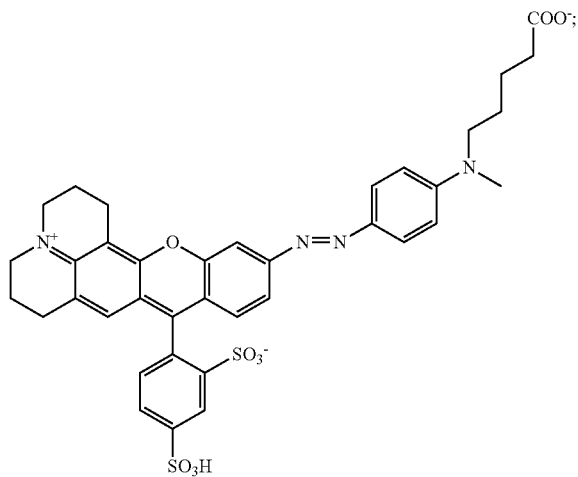

SR101-Q-N₃

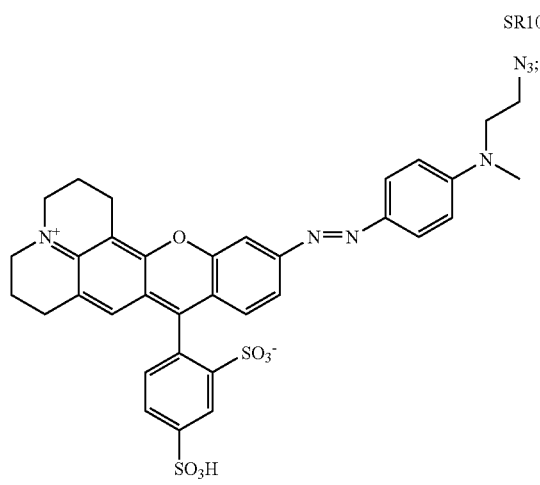

SR101-Q-CCH

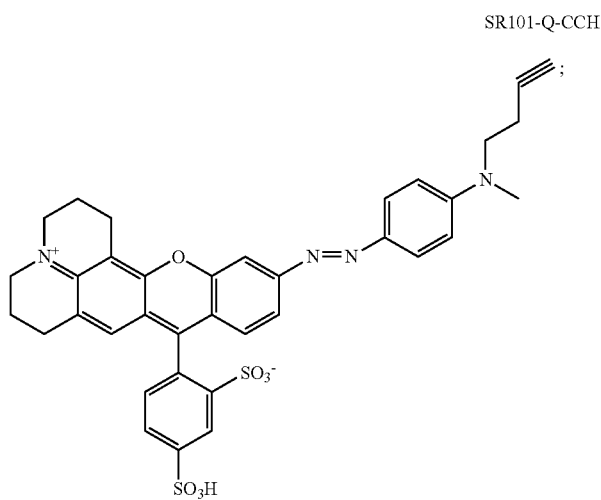

61
-continued
SR101-Q-Mal
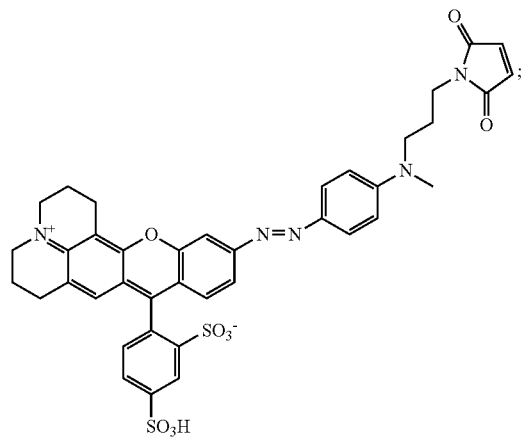
SR101-Q-NH₂
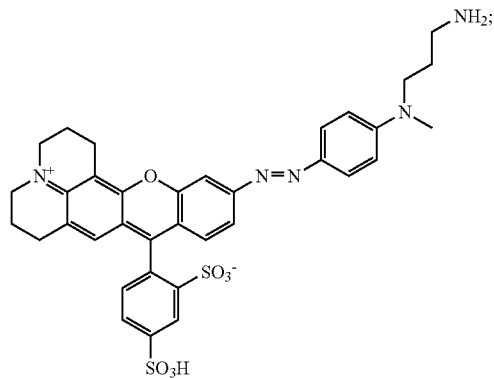
62
SR101-NaphtNH₂-Hyp
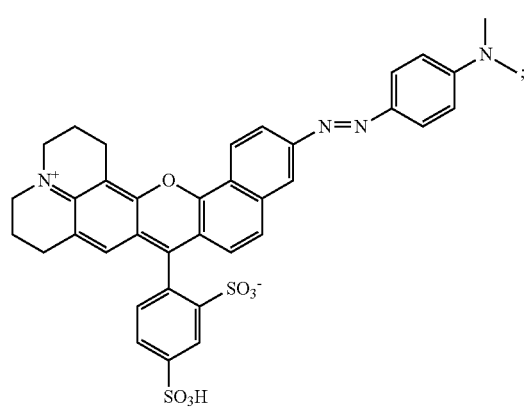
SR101-NaphtNH₂-Hyp-(N₃)₂
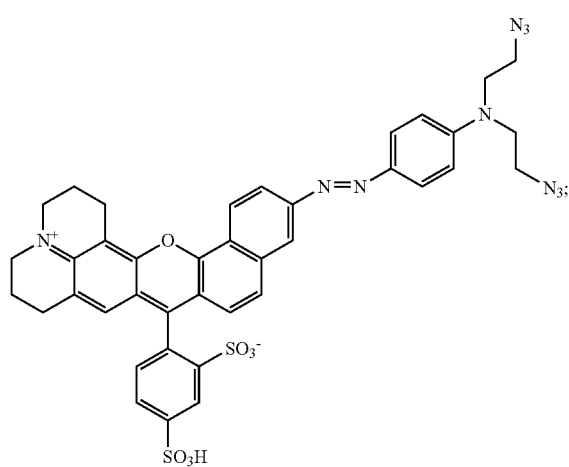

SR101-NaphtNH₂-Hyp-Sulfobetain
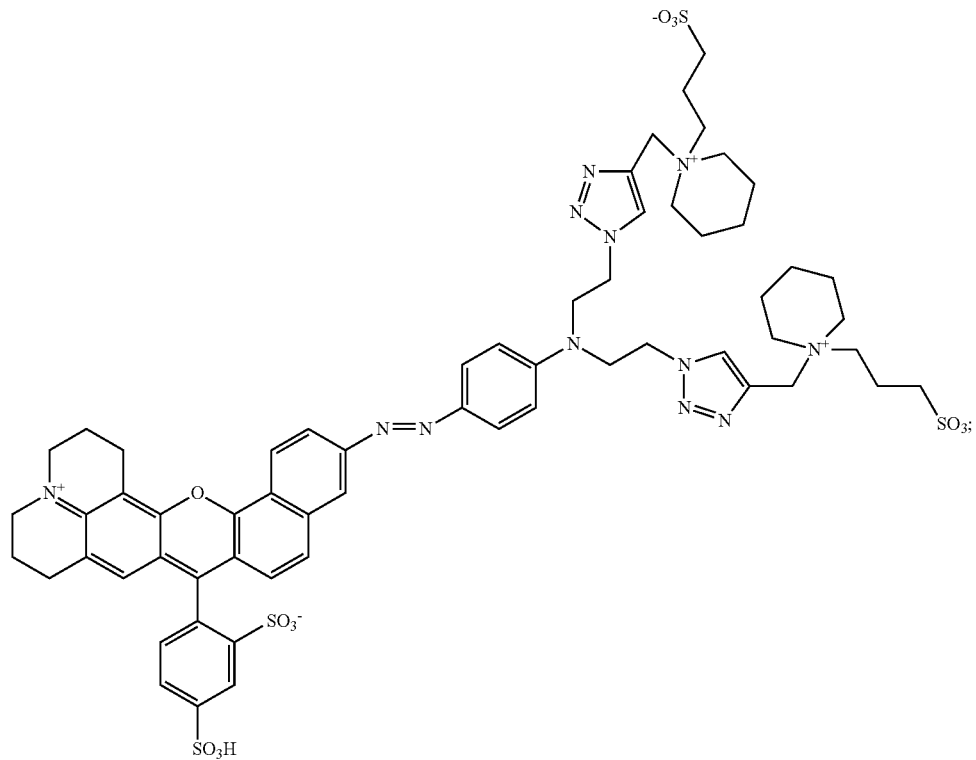
SR101-NaphtNH₂-Hyp-Ammonium
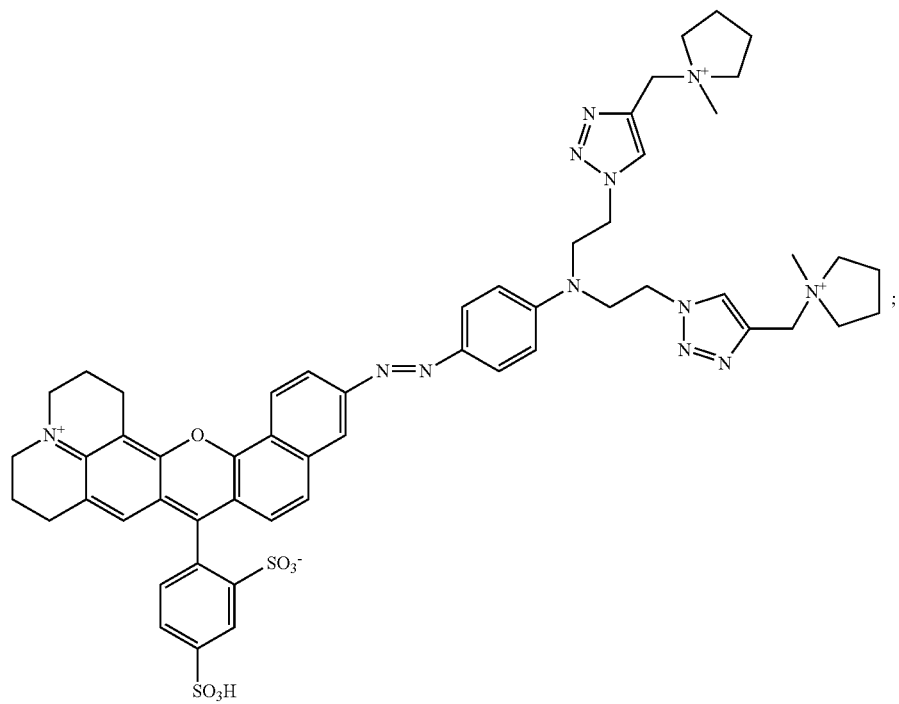

-continued
SR101-OAc
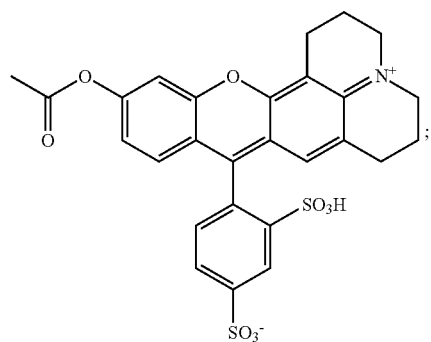
SR101-NaphtOAc
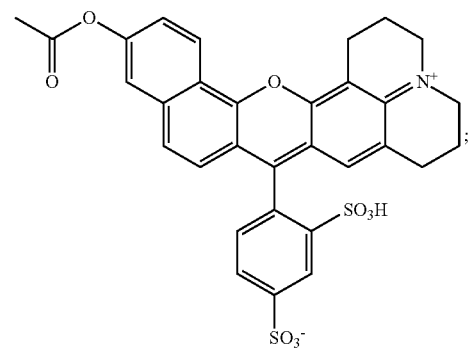
SR101-NaphtO-lauric acid
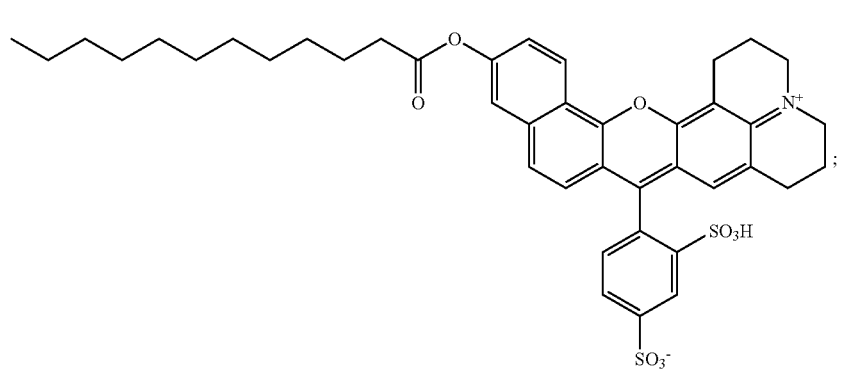
SR101-NaphtO(SO$_3$H)
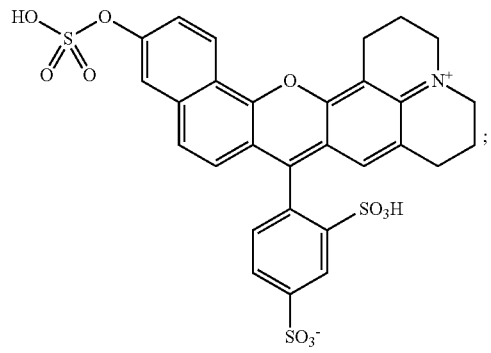
SR101-NaphtO(PO)(OBn)$_2$
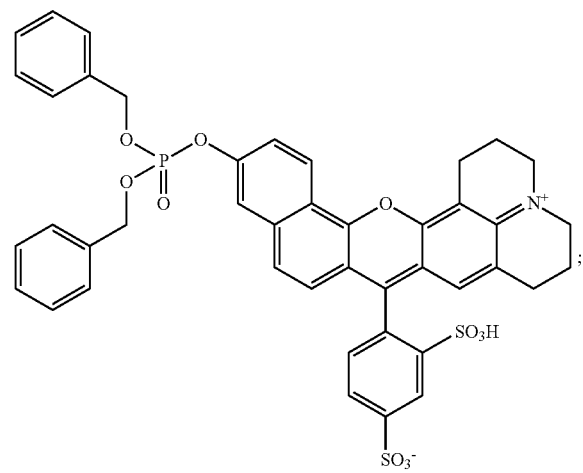
SR101-NaphtO(PO$_3$H$_2$)
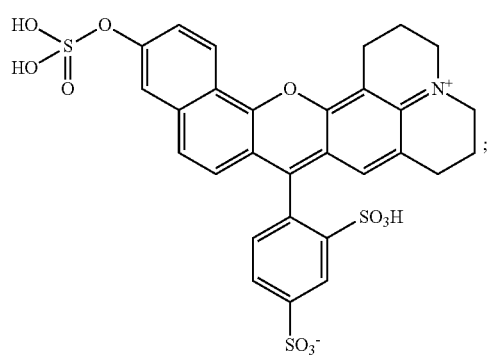
SR101-NHAc
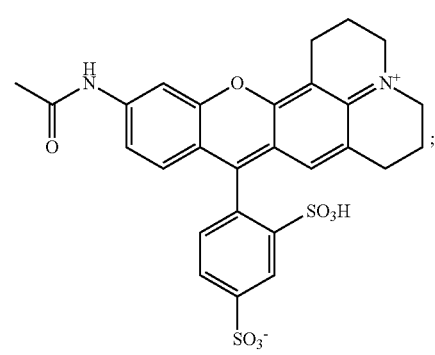

-continued
Gly-SR101-110
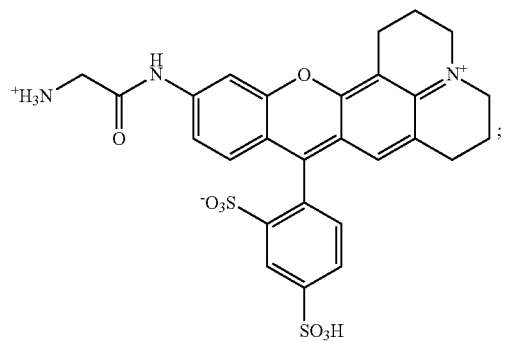
β-Ala-SR101-110
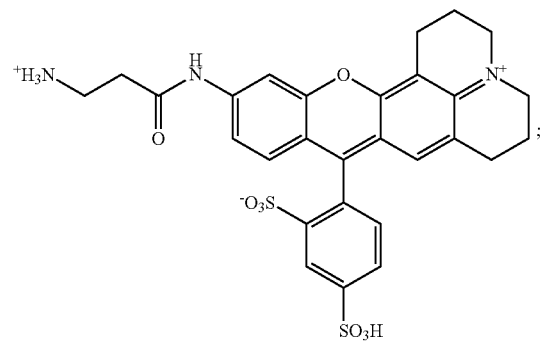
L-Pyr-SR101-110
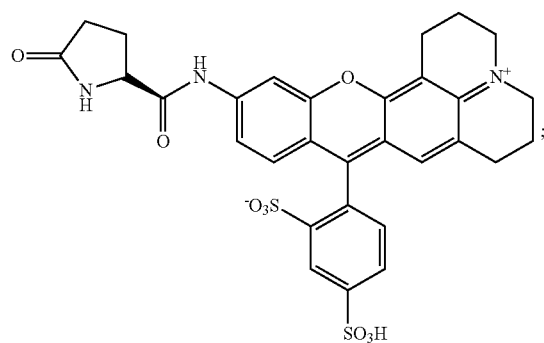
L-Pro-SR101-110
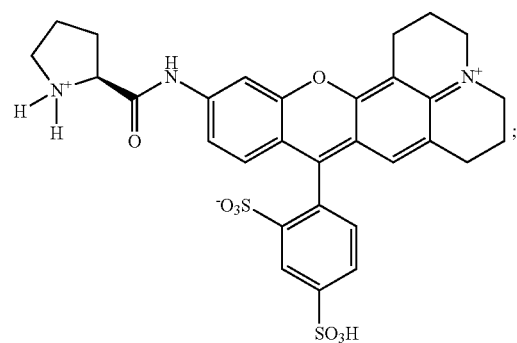
SR101-NaphtO(para-aminophenyl)
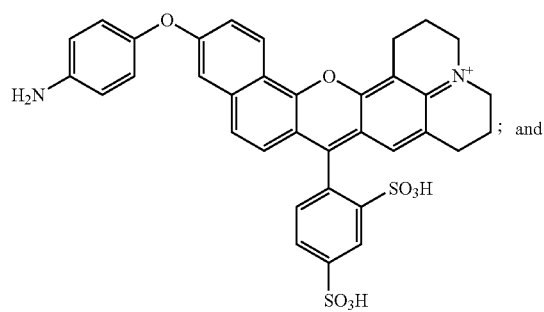; and
SR101-NaphtO(para-nitrophenyl)
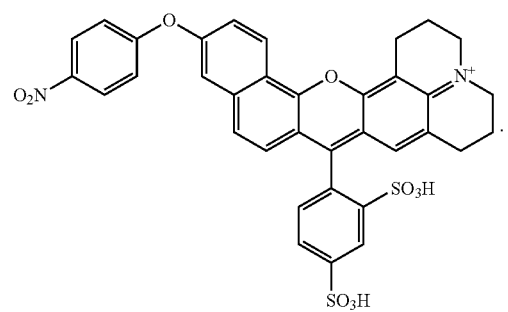.

13. A method for detecting an enzymatic activity of a microorganism selected from the group consisting of nitroreductase, azoreductase, peptidase, glycosidase, esterase and myeloperoxidase activities, the method comprising:

detecting formation of a fluorescent reporter molecule of formula I' or II' as a result of a fluorogenic substrate of formula I or II being subjected to the enzymatic activity of the microorganism:

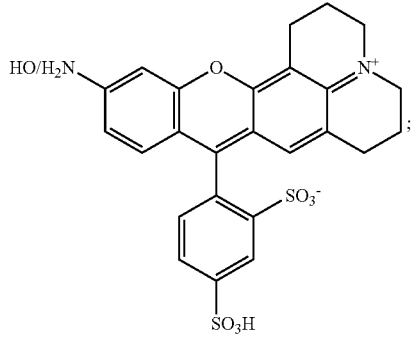
(I')

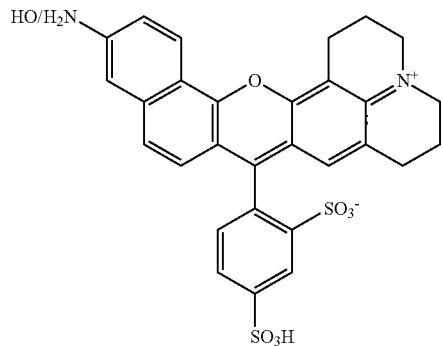
(II'')

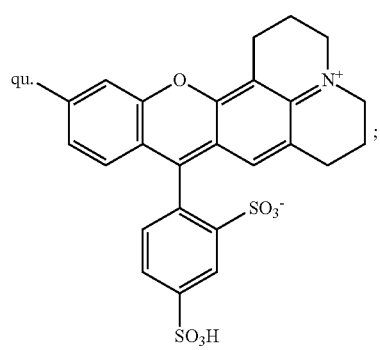
(I)

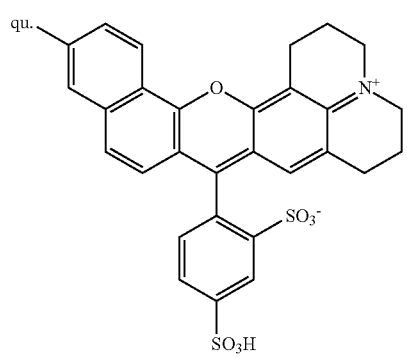
(II)

wherein qu. is a fluorescence quencher group selected from the group consisting of:

—$NO_2$;
—N=N—$R^1$; $R^1$ being any organic group that does not obscure the corresponding azo bond;
—NHCO-Pept.; Pept. being a peptide residue or any organic group that does not obscure the corresponding amide bond;
—O-Glyc.; Glyc. being an oligoglycoside residue that does not obscure the corresponding glycosidic bond;
—O—C(O)—$R^2$; —O—P(O)($OR^2$)($OR^{2'}$) and —O—S($O)_2$—$R^2$; $R^2$ and $R^{2'}$ being independently a hydrogen atom or any organic group that does not obscure the corresponding ester bond; and

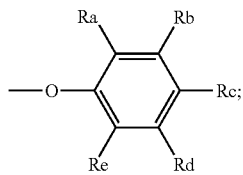

$R_a$, $R_b$, $R_c$, $R_d$ and $R_e$ being independently a hydrogen atom or any organic group that does not obscure the corresponding arylether bond.

14. The method of claim 13, wherein qu. is —$NO_2$ and the enzyme activity to detect is a nitroreductase activity.

15. The method of claim 13, wherein qu. is —N=N—$R^1$ and the enzyme activity to detect is an azoreductase activity.

16. The method of claim 13, wherein qu. is —O—C(O)—$R^2$;
—O—P(O)($OR^{2'}$) or —O—S($O)_2$—$R^2$, and the enzyme activity to detect is a carboxylesterase, a phosphoesterase or a sulfoesterase activity.

17. The method of claim 13, wherein qu. is

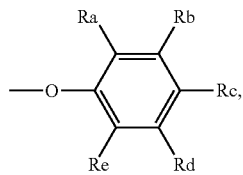

and the enzyme activity to detect is a myeloperoxidase activity.

18. The method of claim 6, wherein qu. is —$NO_2$ and the enzyme activity to detect is a nitroreductase activity.

19. The method of claim 6, wherein qu. is —N=N—$R^1$ and the enzyme activity to detect is an azoreductase activity.

20. The method of claim 6, wherein qu. is —O—C(O)—$R^2$;
—O—P(O)($OR^{2'}$) or —O—S($O)_2$—$R^2$, and the enzyme activity to detect is a carboxylesterase, a phosphoesterase or a sulfoesterase activity.

21. The method of claim 6, wherein qu. is

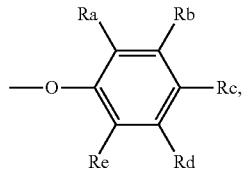

and the enzyme activity to detect is a myeloperoxidase activity.

* * * * *